(12) United States Patent
Korus et al.

(10) Patent No.: US 11,918,734 B2
(45) Date of Patent: Mar. 5, 2024

(54) VAPOR PROVISION SYSTEM WITH AEROSOLISABLE SUBSTRATE MATERIAL CARRYING PORTION DETECTION

(71) Applicant: Nicoventures Trading Limited, London (GB)

(72) Inventors: Anton Korus, London (GB); Justin Han Yang Chan, London (GB); Patrick Moloney, London (GB)

(73) Assignee: NICOVENTURES TRADING LIMITED, London (GB)

( * ) Notice: Subject to any disclaimer, the term of this patent is extended or adjusted under 35 U.S.C. 154(b) by 769 days.

(21) Appl. No.: 15/733,688

(22) PCT Filed: Mar. 27, 2019

(86) PCT No.: PCT/GB2019/050869
§ 371 (c)(1),
(2) Date: Sep. 29, 2020

(87) PCT Pub. No.: WO2019/186150
PCT Pub. Date: Oct. 3, 2019

(65) Prior Publication Data
US 2021/0022403 A1    Jan. 28, 2021

(30) Foreign Application Priority Data

Mar. 29, 2018 (GB) ...................................... 1805192
Jan. 28, 2019 (GB) ...................................... 1901115

(51) Int. Cl.
*A61M 11/04*     (2006.01)
*A24F 40/10*     (2020.01)
(Continued)

(52) U.S. Cl.
CPC ........... *A61M 11/042* (2014.02); *A24F 40/42* (2020.01); *A24F 40/50* (2020.01); *A24F 40/51* (2020.01);
(Continued)

(58) Field of Classification Search
CPC ........ A61M 11/042; A61M 2016/0015; A61M 2016/003; A61M 2205/6018;
(Continued)

(56) References Cited

U.S. PATENT DOCUMENTS

| 9,549,573 | B2 | 1/2017 | Monsees et al. |
| 11,064,741 | B2 * | 7/2021 | Reevell ............... H05B 1/0244 |

(Continued)

FOREIGN PATENT DOCUMENTS

| EP | 2399636 A1 | 12/2011 |
| WO | WO-2013060781 A1 | 5/2013 |

(Continued)

OTHER PUBLICATIONS

International Preliminary Report on Patentability for Application No. PCT/GB2019/050869, dated Oct. 8, 2020, 9 pages.

(Continued)

*Primary Examiner* — Edwin A. Leon
(74) *Attorney, Agent, or Firm* — BURR & FORMAN LLP

(57) ABSTRACT

An electronic vapor provision system includes a control unit configured to provide power from a battery in the control unit to components of the system, and including a controller configured to control components of the system; and an aerosolizable substrate material carrying portion separably connectable to the control unit to obtain power from the battery, and including a first electrical circuit including a characteristic-carrying element; and a second electrical circuit including a vapor generating element configured to (Continued)

generate an inhalable vapor from an aerosolizable substrate material; wherein: the second electrical circuit can be selectively provided with power from the battery when power is supplied to the aerosolizable substrate material carrying portion; and the controller is configured to operate in a first mode in which a characteristic of the characteristic-carrying element is determined by providing power from the battery to the first electrical circuit, and in a second mode in which the vapor generating element is operated by providing power from the battery to the second electrical circuit.

20 Claims, 8 Drawing Sheets

(51) Int. Cl.

| | |
|---|---|
| *A24F 40/42* | (2020.01) |
| *A24F 40/50* | (2020.01) |
| *A24F 40/51* | (2020.01) |
| *A24F 40/53* | (2020.01) |
| *H03K 17/687* | (2006.01) |

(52) U.S. Cl.
CPC .......... *A24F 40/53* (2020.01); *H03K 17/687* (2013.01); *A24F 40/10* (2020.01)

(58) Field of Classification Search
CPC .. A61M 2205/6027; A61M 2205/6036; A61M 2205/8206; A61M 15/06; A61M 11/005; A24F 40/42; A24F 40/50; A24F 40/51; A24F 40/53; A24F 40/10; H03K 17/687
See application file for complete search history.

(56) References Cited

U.S. PATENT DOCUMENTS

| | | | | |
|---|---|---|---|---|
| 2014/0014126 | A1 | 1/2014 | Peleg et al. | |
| 2014/0270727 | A1* | 9/2014 | Ampolini | A24F 40/50 392/394 |
| 2014/0338685 | A1* | 11/2014 | Amir | H05B 1/0244 131/329 |
| 2015/0208731 | A1* | 7/2015 | Malamud | H05B 1/0244 131/328 |
| 2017/0013879 | A1 | 1/2017 | Frisbee et al. | |
| 2017/0048371 | A1 | 2/2017 | Murison et al. | |

FOREIGN PATENT DOCUMENTS

| | | | |
|---|---|---|---|
| WO | WO-2014071329 | A1 | 5/2014 |
| WO | WO-2017021550 | A1 | 2/2017 |
| WO | WO-2017137138 | A1 | 8/2017 |
| WO | WO-2017163045 | A1 | 9/2017 |

OTHER PUBLICATIONS

International Search Report and Written Opinion for Application No. PCT/GB2019/050869, dated Jun. 14, 2019, 11 pages.

* cited by examiner

VAPOR PROVISION SYSTEM WITH AEROSOLISABLE SUBSTRATE MATERIAL CARRYING PORTION DETECTION

PRIORITY CLAIM

The present application is a National Phase entry of PCT Application No. PCT/GB2019/050869, filed Mar. 27, 2019, which claims priority from GB Patent Application No. 1805192.0, filed Mar. 29, 2018, and GB Patent Application No. 1901115.4, filed Jan. 28, 2019 each of which is hereby fully incorporated herein by reference.

TECHNICAL FIELD

The present disclosure relates to apparatus and methods for detecting an aerosolizable substrate material carrying portion of an electronic vapor provision system.

BACKGROUND

Many electronic vapor provision systems, such as e-cigarettes and other electronic nicotine delivery systems that deliver nicotine via vaporized liquids, and hybrid devices which additionally include a portion of tobacco or other flavor element through which vapor generated from a liquid is passed, are formed from two main components or sections, namely a cartomizer and a control unit (power or battery section). The cartomizer generally includes a reservoir of liquid and an atomizer for vaporizing the liquid. These parts may collectively be designated as an aerosol source. The atomizer may be implemented as an electrically resistive vapor generating element such as heating wire formed into a coil or other shape, and a wicking element in proximity to the heater which transports liquid from the reservoir to the vapor generating element. The control unit generally includes a battery for supplying power to the vapor generating element and other items in the cartomizer under the control of a controller. Electrical power from the battery is delivered to the vapor generating element, which heats up or otherwise operates to vaporize liquid delivered by the wicking element from the reservoir. The vaporized liquid is then inhaled by the user.

The cartomizer may be intended as a disposable component to be replaced when the reservoir, having been pre-filled during manufacture of the cartomizer, becomes empty. A wide variety of liquids are known, with different flavors, nicotine strengths and other characteristics. Also, the atomizer may be configured for a particular operation, regarding level and duration of vapor production and other operational parameters. Hence, a range of cartomizers may be made available, each model able to provide a different vapor or vapor inhalation experience. In some cases, vapor production from a particular cartomizer will require appropriate operation of the control unit, for example the delivery of a correct amount of electrical power to the vapor generating element. Accordingly, it can be useful for a control unit to be able to identify a cartomizer to which it is attached in order to enable accurate and safe operation of the vapor provision system.

SUMMARY

According to a first aspect of some embodiments described herein, there is provided an electronic vapor provision system comprising: a control unit configured to provide power from a battery in the control unit to components of the system, and comprising a controller configured to control components of the system; and an aerosolizsable substrate material carrying portion separably connectable to the control unit to obtain power from the battery, and comprising: a first electrical circuit including a characteristic-carrying element; and a second electrical circuit including a vapor generating element configured to generate an inhalable vapor from an aerosolizsable substrate material; wherein: the second electrical circuit can be selectively provided with power from the battery when power is supplied to the aerosolizsable substrate material carrying portion; and the controller is configured to operate in a first mode in which a characteristic of the characteristic carrying element is determined by providing power from the battery to the first electrical circuit, and in a second mode in which the vapor generating element is operated by providing power from the battery to the second electrical circuit.

According to a second aspect of some embodiments described herein, there is provided an aerosolizsable substrate material carrying portion for an electronic vapor provision system, separably connectable to a control unit to obtain power from a battery within the control unit, and comprising: a first electrical circuit including a characteristic-carrying element; and a second electrical circuit including a vapor generating element configured to generate an inhalable vapor from an aerosolizsable substrate material when provided with power from the battery; wherein the second electrical circuit can be selectively provided with power from the battery when power is supplied to the aerosolizsable substrate material carrying portion for the purpose of operating in a first mode in which a characteristic of the characteristic-carrying element is determined when power is provided from the battery to the first electrical circuit, and for the purpose of operating in a second mode in which the vapor generating element is operated when power is provided from the battery to the second electrical circuit.

According to a third aspect of some embodiments described herein, there is provided a control unit for an electronic vapor provision system which is separably connectable to an aerosolizsable substrate material carrying portion comprising a first electrical circuit including a characteristic-carrying element and a second electrical circuit including a vapor generating element configured to generate an inhalable vapor from an aerosolizsable substrate material, the second electrical circuit selectively providable with power from the battery when power is supplied to the aerosolizsable substrate material carrying portion, the control unit configured to provided power from a battery in the control unit to components of the vapor provision system, and comprising: a controller configured to control components of the system and to operate in a first mode in which power is provided from the battery to the first electrical circuit to determine a characteristic of the characteristic-carrying element, and to operate in a second mode in which power is provided from the battery to the second electrical circuit to operate the vapor generating element.

According to a fourth aspect of some embodiments described herein, there is provided a controller for an electronic vapor provision system comprising a control unit and an aerosolizsable substrate material carrying portion separably connectable to the control unit, the controller configured to: provide power from a battery in the control unit to a first electrical circuit in the aerosolizsable substrate material carrying portion including a characteristic-carrying element and to a second electrical circuit in the aerosolizsable substrate material carrying portion including a vapor generating element configured to generate an inhalable vapor from an aerosolizsable substrate material; determine a characteristic of the characteristic-carrying element when power is provided to the first electrical circuit; and operate the vapor generating element when power is provided to the second electrical circuit.

According to a fifth aspect of some embodiments described herein, there is provided a method of operating an electronic vapor provision system comprising: connecting an aerosolizsable substrate material carrying portion to a control unit; providing power from a battery in the control unit to a first electrical circuit in the aerosolizsable substrate material carrying portion, the first electrical circuit including a characteristic-carrying element; determining a characteristic of the characteristic-carrying element; deducing an identity or property of the aerosolizsable substrate material carrying portion from the characteristic; and providing power from the battery in the control unit to a second electrical circuit in the aerosolizsable substrate material carrying portion including a vapor generating element to operate the vapor generating element to generate an inhalable vapor from an aerosolizsable substrate material.

According to a sixth aspect of some embodiments described herein, there is provided an electronic vapor provision system comprising: a control unit configured to provide power from a battery in the control unit to components of the system, and comprising a controller configured to control components of the system; and an aerosolizsable substrate material carrying portion separably connectable to the control unit to obtain power from the battery, and comprising: a first electrical circuit including an identifier resistor; and a second electrical circuit including a vapor generating element configured to generate an inhalable vapor from an aerosolizsable substrate material; wherein: the second electrical circuit can be selectively provided with power from the battery when power is supplied to the aerosolizsable substrate material carrying portion; and the controller is configured to operate in a first mode in which a resistance value for the identifier resistor is determined by providing power from the battery to the first electrical circuit, and in a second mode in which the vapor generating element is operated by providing power from the battery to the second electrical circuit.

According to a seventh aspect of some embodiments described herein, there is provided an electronic vapor provision system comprising: a control unit configured to provide power from a battery in the control unit to components of the system, and comprising a controller configured to control components of the system; and an aerosolizsable substrate material carrying portion separably connectable to the control unit to obtain power from the battery, and comprising: a first electrical circuit including a readable memory; and a second electrical circuit including a vapor generating element configured to generate an inhalable vapor from an aerosolizsable substrate material; wherein: the second electrical circuit can be selectively provided with power from the battery when power is supplied to the aerosolizsable substrate material carrying portion; and the controller is configured to operate in a first mode in which identity data identifying the aerosolizsable substrate material carrying portion stored in the readable memory is determined by providing power from the battery to the first electrical circuit, and in a second mode in which the vapor generating element is operated by providing power from the battery to the second electrical circuit.

According to an eighth aspect of some embodiment described herein, there is provided an electronic vapor provision system comprising: a control unit configured to provide power from a battery in the control unit to components of the system, and comprising a controller configured to control components of the system; and an aerosolizsable substrate material carrying portion separably connectable to the control unit to obtain power from the battery, and comprising: a first electrical circuit including a readable memory; and a second electrical circuit including a vapor generating element configured to generate an inhalable vapor from an aerosolizsable substrate material; wherein: the second electrical circuit can be selectively provided with power from the battery when power is supplied to the aerosolizsable substrate material carrying portion; and the controller is configured to operate in a first mode in which property data indicating one or more properties of the aerosolizsable substrate material carrying portion stored in the readable memory is determined by providing power from the battery to the first electrical circuit, and in a second mode in which the vapor generating element is operated by providing power from the battery to the second electrical circuit.

Features described herein with reference to example vapor provision systems, cartomizers, control units and controllers are also applicable to example methods.

These and further aspects of the certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, a vapor provision system or part thereof including aerosolizsable substrate material carrying portion detection may be provided in accordance with approaches described herein which includes any one or more of the various features described below as appropriate.

BRIEF DESCRIPTION OF THE DRAWINGS

Various embodiments of the disclosure will now be described in detail by way of example only with reference to the following drawings in which:

FIG. 1 shows a schematic diagram of an example vapor provision system in which the presently disclosed cartomizer detection may be implemented.

FIG. 2 shows a highly schematic representation of parts of a cartomizer and a control unit of a vapor provision system including an example cartomizer detection arrangement.

FIG. 3 shows a schematic representation of parts of a cartomizer and a control unit comprising cartomizer detection using a switching arrangement in the control unit according to some examples.

FIG. 4 shows a schematic representation of parts of a cartomizer and a control unit with a first example switching arrangement in the control unit.

FIG. 5 shows a schematic representation of parts of a cartomizer and a control unit with a second example switching arrangement in the control unit.

FIGS. 6(A) to 6(D) show plan and perspective views of example cartomizers provided with three electrical connection terminals according to some examples.

FIG. 7 shows a schematic representation of parts of a cartomizer and a control unit comprising cartomizer detection using a switching arrangement in the cartomizer according to some examples.

FIG. 8 shows a schematic representation of parts of a cartomizer and a control unit with an example switching arrangement comprising a field-effect transistor in the cartomizer.

DETAILED DESCRIPTION

Figure 1:
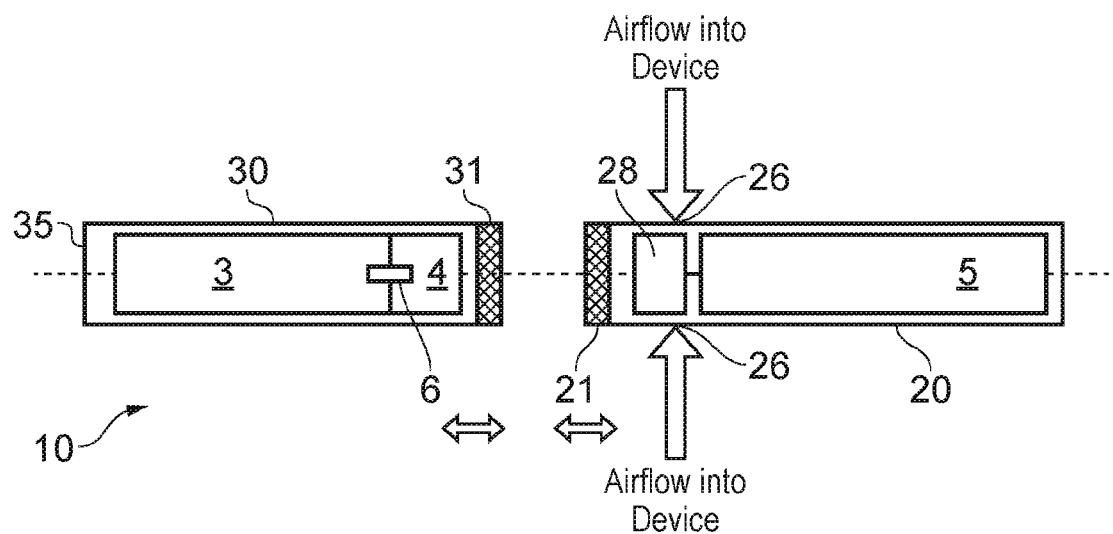

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. The disclosure is also applicable to systems configured to release compounds by heating, but not burning, a solid/gel substrate material. The substrate material may be for example tobacco or other non-tobacco products, which may or may not contain nicotine. In addition, the disclosure is also applicable to hybrid systems configured to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. The term "aerosolizsable substrate material" as used herein is intended to refer to substrate materials which can form an aerosol, either through the application of heat or some other means. The various terms noted above should be understood to include such devices. Similarly, "aerosol" may be used interchangeably with "vapor".

As used herein, the term "component" is used to refer to a part, section, unit, module, assembly or similar of an electronic cigarette that incorporates several smaller parts or elements, often within an exterior housing or wall. An electronic cigarette may be formed or built from one or more such components, and the components may be removably or separably connectable to one another, or may be permanently joined together during manufacture to define the whole electronic cigarette. The present disclosure is particularly concerned with systems comprising two components separably connectable to one another and configured, for example, as an aerosolizsable substrate material carrying portion holding liquid or another aerosolizsable substrate material and an electrically operable element for generating vapor from the substrate material, and a control unit having a battery for providing electrical power to the cartomizer. For the sake of providing a concrete example, in the present disclosure, a cartomizer is described as an example of the aerosolizsable substrate material carrying portion, but the disclosure is not limited in this regard and is applicable to any configuration of aerosolizsable substrate material carrying portion.

FIG. 1 is a highly schematic diagram (not to scale) of an example aerosol/vapor provision system such as an e-cigarette 10. The e-cigarette 10 has a generally elongate shape, extending along a longitudinal axis indicated by a dashed line, and comprises two main components, namely a control or power component, section or unit 20 and a cartridge assembly or section 30 carrying aerosolizsable substrate material and, sometimes referred to as a cartomizer or clearomizer, that operates as a vapor-generating component.

The cartomizer 30 includes a reservoir 3 containing a source liquid or other aerosolizsable substrate material comprising a formulation such a liquid or gel from which an aerosol is to be generated, for example containing nicotine. As an example, the source liquid may comprise around 1 to 3% nicotine and 50% glycerol, with the remainder comprising roughly equal measures of water and propylene glycol, and possibly also comprising other components, such as flavorings. Nicotine-free source liquid may also be used, such as to deliver flavoring. A solid substrate (not illustrated) such as a portion of tobacco or other flavor element through which vapor generated from the liquid is passed, may also be included. The reservoir 3 has the form of a storage tank, being a container or receptacle in which source liquid can be stored such that the liquid is free to move and flow within the confines of the tank. Alternatively, the reservoir 3 may contain a quantity of absorbent material such as cotton wadding, glass fiber or porous ceramic which holds the source liquid within a porous structure. The reservoir 3 may be sealed after filling during manufacture so as to be disposable after the source liquid is consumed, or may have an inlet port or other opening through which new source liquid can be added. The cartomizer 30 also comprises an electrical heating element or heater 4 located externally of the reservoir tank 3 for generating the aerosol by vaporization of the source liquid by heating. A liquid transfer arrangement (liquid transport element) such as a wick or other porous element 6 may be provided to deliver source liquid from the reservoir 3 to the heater 4. The wick 6 has one or more parts located inside the reservoir 3, or otherwise in fluid communication with the liquid in the reservoir 3, so as to be able to absorb source liquid and transfer it by wicking or capillary action to other parts of the wick 6 that are in contact with the heater 4. This liquid is thereby heated and vaporized, to be replaced by new source liquid transferred to the heater 4 by the wick 6. The wick may be thought of as a bridge, path or conduit between the reservoir 3 and the heater 4 that delivers or transfers liquid from the reservoir to the heater. Terms including conduit, liquid conduit, liquid transfer path, liquid delivery path, liquid transfer mechanism or element, and liquid delivery mechanism or element may all be used interchangeably herein to refer to a wick or corresponding component or structure.

A heater and wick (or similar) combination is sometimes referred to as an atomizer or atomizer assembly, and the reservoir with its source liquid plus the atomizer may be collectively referred to as an aerosol source. Other terminology may include a liquid delivery assembly, a liquid transfer assembly, or simply assembly, where in the present context these terms may be used interchangeably to refer to a vapor-generating element (vapor generator) and a wicking or similar component or structure (liquid transport element) that delivers or transfers liquid from a reservoir to the vapor generator. Various designs are possible, in which the parts may be differently arranged compared with the highly schematic representation of FIG. 1. For example, the wick 6 may be an entirely separate element from the heater 4, or the heater 4 may be configured to be porous and able to perform at least part of the wicking function directly (a metallic mesh, for example). Other means for vapor generation may be used in place of a heater, such a vibrating vaporizer based on the piezoelectric effect, for example. In an electrical or electronic device, the vapor generating element may be an electrical heating element that operates by ohmic (Joule) heating or by inductive heating. In general, therefore, an atomizer can be considered to be a vapor-generating or vaporizing element able to generate vapor from source liquid delivered to it, and a liquid transport element able to deliver or transport liquid from a reservoir or similar liquid store to the vapor generator by a wicking action/capillary force. An atomizer is typically housed in a cartomizer component of a vapor generating system. Embodiments of the disclosure are applicable to all and any such assembly configurations where the vapor generating element is electrically operated.

Returning to FIG. 1, the cartomizer 30 also includes a mouthpiece 35 having an opening or air outlet through which a user may inhale the aerosol generated by the heater 4. The power component or control unit 20 includes a cell or battery 5 (referred to herein after as a battery, and which may be re-chargeable) to provide power for electrical components of the e-cigarette 10, in particular the heater 4. Additionally, there is a controller 28 such as a printed circuit board and/or other electronics or circuitry for generally controlling the e-cigarette. The control electronics/circuitry 28 connects the heater 4 to the battery 5 when vapor is required, for example in response to a signal from an air pressure sensor or air flow sensor (not shown) that detects an inhalation on the system 10 during which air enters through one or more air inlets 26 in the wall of the control unit 20. When the heating element 4 receives power from the battery 5, the heating element 4 vaporizes source liquid delivered from the reservoir 3 by the wick 6 to generate the aerosol, and this is then inhaled by a user through the opening in the mouthpiece 35. The aerosol is carried from the aerosol source to the mouthpiece 35 along an air channel (not shown) that connects the air inlet 26 to the aerosol source to the air outlet when a user inhales on the mouthpiece 35.

The control unit (power section) 20 and the cartomizer (cartridge assembly) 30 are separate connectable parts detachable from one another by separation in a direction parallel to the longitudinal axis, as indicated by the solid arrows in FIG. 1. The components 20, 30 are joined together when the device 10 is in use by cooperating engagement elements 21, 31 (for example, a screw or bayonet fitting) which provide mechanical and electrical connectivity between the power section 20 and the cartridge assembly 30. This is merely an example arrangement, however, and the various components may be differently distributed between the power section 20 and the cartridge assembly section 30, and other components and elements may be included. The two sections may connect together end-to-end in a longitudinal configuration as in FIG. 1, or in a different configuration such as a parallel, side-by-side arrangement. The system may or may not be generally cylindrical and/or have a generally longitudinal shape. Either or both sections or components may be intended to be disposed of and replaced when exhausted (the reservoir is empty or the battery is flat, for example), or be intended for multiple uses enabled by actions such as refilling the reservoir and recharging the battery. Embodiments and examples of the present disclosure are applicable to any of these configurations and other configurations of which the skilled person will be aware.

A range of different cartomizers may be made available which are suitable for use with a particular design of control unit. For example, characteristics of a liquid or other aerosolizsable substrate material such as flavor or nicotine strength with which the reservoir of the cartomizer is pre-filled may be varied. The operational specification of parts within the cartomizer may be varied, such as configuration of an atomizer to provide more or less vapor, for example. Other ranges of different cartomizers may be made available for use with other control unit designs. Cartomizers may be offered by the same manufacturer as the manufacturer of the control unit, or by one or more other manufacturers. Hence a large selection of differently configured cartomizers with one or more differing attributes, features or properties may be available for use. Cartomizers with different attributes and features may be designated as different models of cartomizer. Two cartomizers of the same design and configuration with matching attributes features and properties are considered to be the same model. Two cartomizers of different design, or of the same design with one or more differing features or attributes are considered to be different models. Each model can be considered as having a unique identity.

It may be useful for the model or identity of a cartomizer to be made available to a control unit to which the cartomizer is connected for use. This can enable the control unit to provide appropriate control signals and power levels for safe and accurate operation of the cartomizer, and may be used to prevent cartomizer operation if it is found that the cartomizer is not appropriately configured for operation with the particular control unit. For example, it may be an incompatible model, or may be a counterfeit or unlicensed cartomizer product from a different manufacturer. Accordingly, the present disclosure presents arrangements by which a control unit is configured to detect a characteristic of a cartomizer from which the model of the cartomizer, or other information about the cartomizer, may be deduced. Usefully, the characteristic is a resistance value of a resistor comprised within the cartomizer for the purpose of enabling cartomizer model identification.

This is merely an example, however. More generally, the cartomizer comprises a element that carries a characteristic, in other words, a characteristic-carrying element. The element can be addressed, read, accessed or otherwise interrogated by the provision of electrical power to it, in order to obtain a value or other indication of the characteristic. Information about the cartomizer, such as its identity, is determinable from the characteristic. For example, an alternative form of characteristic-carrying element to the resistor noted above is a readable memory which stores data and can be read by the application of electrical power to the memory. The data can comprise one or more characteristics. For example, the characteristic carried by the readable memory may be identifier data from which the cartomizer model can be identified, similar to the use of a resistor with a resistance value mentioned above. More generally, the data might be property data that indicates other properties of the cartomizer, instead of or as well as the identifier data. The properties might be, for example, information about the cartomizer manufacturer, information about a cartomizer manufacturing batch that includes the cartomizer, location information, information about the aerosolizsable substrate material such as type or remaining amount, and/or other information useful for enabling accurate, successful and safe operation of the vapour provision system that will be apparent to the skilled person. Other elements may be used for the characteristic-carrying element also; any component from which information can be extracted by the application of electrical power can be utilized.

Figure 2:
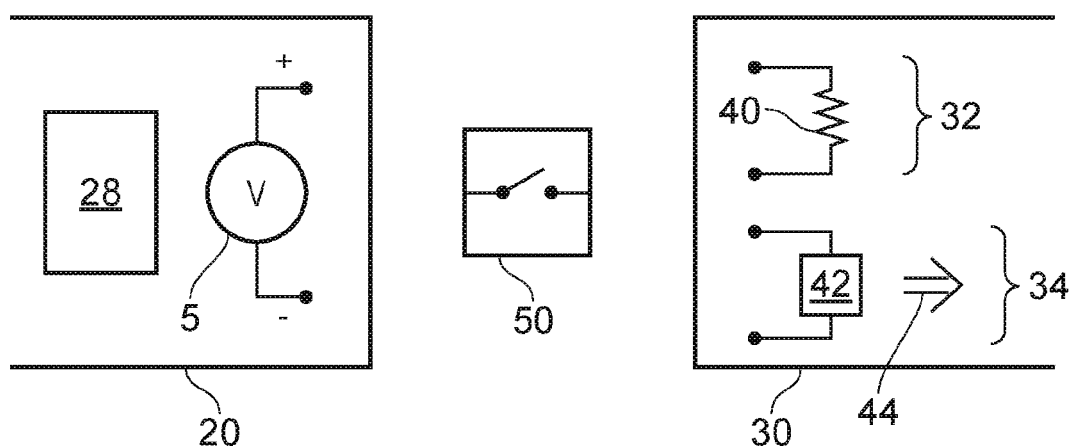

FIG. 2 shows a highly schematic representation of a vapor provision system configured for cartomizer detection and model identification. Electronic components are represented, but most connections between the components are not indicated for simplicity. The system comprises a control unit 20, which will typically be reusable for powering a succession of cartomizers. The control unit 20 comprises a power source 5, such as a battery, for providing electrical power (current, voltage) to electrical items in a cartomizer connected to the control unit 20. Also, the control unit 20 includes a controller 28 for controlling the operation of items in the control unit 20 and in a cartomizer connected to the control unit 20. In particular, the controller 28 can determine levels and timings of the provision of electrical power from the battery 5, can send control signals to operate various electrical items in the vapor provision system, and can receive signals from such items by which control signals and power provision can be generated and regulated. The controller 28 can be implemented as any combination of hardware, software and firmware, and may include one or more processors, and/or electric circuits or circuitry, and memory storing software for implementation by the processor(s) and data used by the processors in determining operation of the vapor provision system. The controller may comprise a printed circuit board, for example.

A cartomizer 30 is connectable to the control unit 20 via a physical and electrical connection which allows the provision of electrical power from the battery 5 to items in the cartomizer 30. The cartomizer includes (among other parts which are not shown for simplicity) two electrical circuits. A first circuit 32 includes an electrically resistive element 40, usefully a conventional resistor. The resistor 40 has a known value of electrical resistance. This value is selected by the provider/manufacturer/designer of the vapor provision system to uniquely represent the model of the cartomizer 30 (or in some examples a particular attribute of the cartomizer model, as discussed further below). All other cartomizers with identical attributes are provided with a resistor 40 having the same resistance value. Other models of cartomizer with different attributes are each provided with a resistor having a different resistance value that represents the appropriate model.

A second circuit 34 includes an atomizer 42 comprising an electrically-powered vapor generating element (such as a heater or a vibrating plate) for generating vapor 44 from liquid in a reservoir.

A switching arrangement 50 is interposed between the battery 5 in the control unit 20 and the resistor 40 and the atomizer 42 in the cartomizer. The switching arrangement 50, which may take a variety of forms as detailed below, is configured to allow electrical power to be provided from the battery 5 individually to the first electrical circuit 32 and/or the second electrical circuit 34 as required when the control unit 20 and the cartomizer 30 are connected. The switching arrangement 50 is under the control of the controller 28.

The first electrical circuit 32 includes the resistor 40 with a resistance value unique to the model of the cartomizer 30; the resistor 40 can be designated as an identifier resistor since it provides the cartomizer 30 with a characteristic from which the identity (model) of the resistor can be deduced.

When it is desired that the cartomizer model be determined, such as when a new cartomizer is connected to the control unit 20, the controller 28 is configured to provide electrical power to the first circuit 32 via a first configuration of the switching arrangement 50, and determine the resistance value of the resistor 40. This can be done in any convenient manner, typically by activation of the battery 5 to pass a known current I through the resistor 40 and measurement of the voltage drop V across the resistor 40, or by applying a known voltage V across the resistor 40 and measuring the current I drawn by the resistor 40, and calculating the resistance using Ohm's law, V=IR, or R=V/I, where R is the resistance value of the resistor 40. The controller 28 is further configured to deduce a model of the cartomizer from the resistance value, such as by consulting a look-up table stored in memory in the control unit 20 (or remotely for access via a wireless connection implemented in the vapor provision system), where the look-up table maps resistance values to cartomizer models. Some or all of the processing required to deduce the model may be performed by the controller 28 on board the electronic cigarette, or by a remote processor accessed by the controller 28, or shared between the controller and a remote processor.

The second electrical circuit 34 enables operation of the vapor provision system to provide vapor. When it is desired for vapor to be generated, such as by operation of a user switch on the system or in response to detection of a puff (inhalation) by an air flow sensor or air pressure sensor in the system, the controller 28 is configured to provide electrical power to the second circuit 34 via a second configuration of the switching arrangement 50 to activate the vapor generating element in the atomizer 42 to generate vapor 44 for inhalation by the user. Note that the second configuration of the switching arrangement may provide power to the second circuit only, with no power going to the first circuit, or it may provide power to the second circuit in addition to the first circuit. More generally, therefore (and as will be appreciated from later examples), the electrical power is selectively provided according to a first mode or a second mode. The first mode includes the supply of power to the first electrical circuit for the purpose of determining the resistance value of the identifier resistor. The second mode includes the supply of power to the second electrical circuit for the purpose of operating the atomizer, and may also include the supply of power to the first electrical circuit, but without any corresponding action to determine the value of the identifier resistor. The switching arrangement may divert power to one circuit or the other circuit to enable the required mode, or may act to additionally deliver power to the second circuit while continuing to supply power to the first circuit when activating the second mode from the first mode.

Provision of electrical power to the second electrical circuit 34 may be controlled by the controller 28 in response to the cartomizer model which has been identified by accessing the first electrical circuit. This information may enable the controller 28 to select an appropriate level, duration or profile of the electrical power to provide to the vapor generating element for effective vapor generation from the liquid and the atomizer 42 included in the cartomizer, for example. Also, if the cartomizer model is found to be incompatible with the control unit, or if identification of the model has been unsuccessful, the controller 28 may be configured to disable operation of the cartomizer 30, or otherwise not provide any electrical power from the battery 5 to the second electrical circuit 34. This can include not placing the switching arrangement 50 into the second configuration, to prevent the supply of electrical power to the second electrical circuit 34.

FIG. 2 shows the first electrical circuit 32 and the second electrical circuit 34 as being entirely separate, each having its own points of electrical connection for receiving electrical power from the battery 5 of a connected control unit 20. This physical configuration is not essential however. Rather, the circuits are configured such that it is possible for the identifier resistor 40 and the atomizer 42 including the vapor generating element to be separately addressable by the battery 5, in other words, that one or other circuit can be provided with electrical power from the battery 5, or energized, individually or independently of the other circuit. In some examples, the first circuit and the second circuit can be addressed one at time only, and cannot both be provided with electrical power at the same time. This separate addressing may be sequential, for example, such that the first electrical circuit 32 is energized when a cartomizer 30 is first connected to the control unit 20, and afterwards the second electrical circuit 34 is energized as often as is required to generate vapor, until the cartomizer 30 is separated from the control unit 20. The first electrical circuit 32 may be addressed during this period also, if it is necessary to repeat verification of the cartomizer identity, between operations of the atomizer 42. This addressing of one or other of the first electrical circuit 32 and the second electrical circuit 34 is achieved by use of the switching arrangement 50. The first electrical circuit 32 and the second electrical circuit 34 may share one or more electrical connection terminals (for making an electrical connection between the cartomizer 30 and the control unit 20). The first electrical circuit includes the identifier resistor 40 and those connection terminals by which electrical power is provided to the resistor 40. The second electrical circuit includes the vapor generating element of the atomizer 42 and those connection terminals by which electrical power is provided to the atomizer 42.

Figure 3:
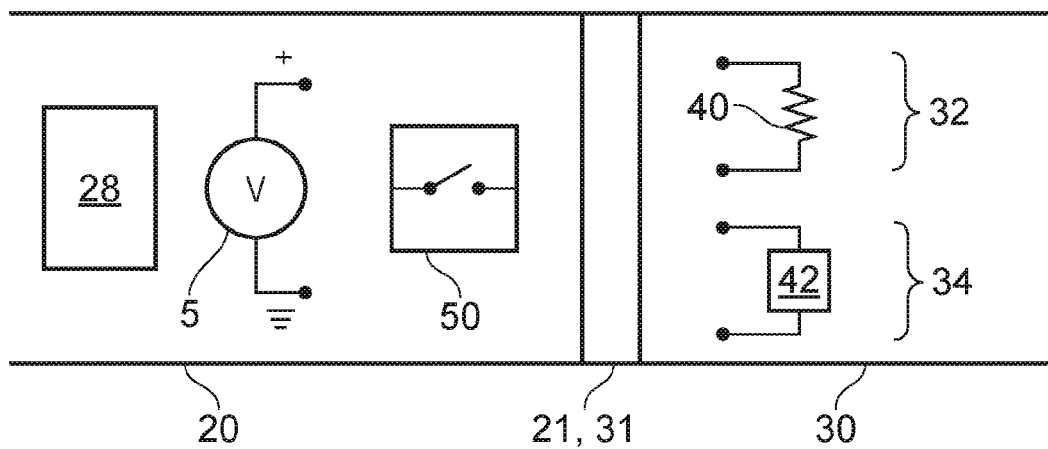

In some examples, the switching arrangement 50 is included within the control unit 20. FIG. 3 shows a schematic representation of a vapor provision system configured with the switching unit 50 located in the control unit 20, and configured (by way of electrical connections which are not shown) to couple the battery 5 to either one of the first electrical circuit 32 or the second electrical circuit 34 in the cartomizer 30. This is achieved when the control unit 20 is attached to this cartomizer 30 using the mechanical and electrical cooperating engagement elements 21, 31, whereupon the controller 28 controls the switching arrangement 50 to make the appropriate connection of the battery 5 to the cartomizer 30 according to which of the first or second electric circuits 40, 42 is required to be operational.

Under such a configuration in which the switching arrangement 50 is inside the control unit 20, the first electrical circuit 32 and the second electrical circuit 34 may be implemented using three electrical connection terminals on the cartomizer for connection with three electrical connection terminals on the control unit when the cartomizer and the control unit are connected for operation of the vapor provision system. One of the three terminals is shared by the two electrical circuits. The switching arrangement 50 is placed in the control unit 20 under control of the controller 28, and is configured to be switched between a first configuration that directs power from the battery to a first electrical connection terminal and the shared terminal to provide power to the first electrical circuit, and a second configuration that directs power from the battery to a second electrical connection terminal and the shared terminal to provide power to the second electrical circuit.

Figure 4:
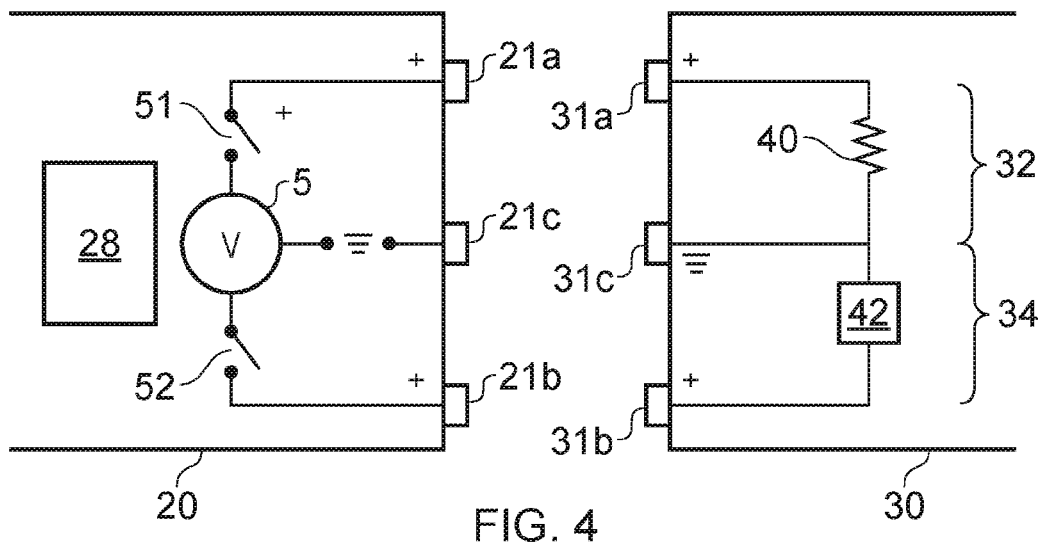

FIG. 4 shows a schematic representation of a first example vapor provision system configured for operation via three electrical connection terminals, the switching arrangement located in the control unit. The cartomizer 30 has three electrical connection terminals 31*a*-31*c* positioned to connect to three corresponding electrical connection terminals 21*a*-21*c* on the control unit 20 when the cartomizer 30 is attached to the control unit 20. A first electrical connection terminal 31*a* on the cartomizer 30 is a positive terminal for the first electrical circuit 40. A second electrical connection terminal 31*b* on the cartomizer 30 is a positive terminal for the second electrical circuit 42. A third electrical connection terminal 31*c* is connected to both the resistor 40 in the first electrical circuit 32 and the atomizer 42 in the second electrical circuit 34, and forms a common or shared negative or ground (earth) terminal. Hence the first electrical circuit 32 comprises the identifier resistor 40 in series between the first electrical connection terminal 31*a* and the third electrical connection terminal 31*c*, and the second electrical circuit 34 comprises the vapor generating element of the 42 in series between the second electrical connection terminal 31*b* and the third electrical connection terminal 31*c*.

The control unit 20 comprises corresponding first, second and third electrical connection terminals 21*a*, 21*b* and 21*c*. The switching arrangement comprises in this example a pair of switches 51, 52, between which the battery 5 is connected. The other side of the first switch 51 is connected to the first electrical connection terminal 21*a* and the other side of the second switch 52 is connected to the second electrical connection terminal 21*b*. Therefore, when the first switch 51 is closed, a voltage is made available between the first and third electrical connection terminals 21*a*, 21*c* of the control unit 20, and when the cartomizer is attached to connect the first terminal 21*a* of the control unit 20 to the first terminal 31*a* of the cartomizer 30 and the third terminal 21*c* of the control unit 20 to the third terminal 31*c* of the cartomizer 30, the first electrical circuit 40 is completed so the resistor 40 receives power from the battery 5. When the second switch is closed, a voltage is made available between the second and third electrical connection terminals 21*b*, 21*c* of the control unit 20, and when the cartomizer is attached to connect the second terminal 21*b* of the control unit 20 to the second terminal 31*b* of the cartomizer 30 and the third terminal 21*c* of the control unit 20 to the third terminal 31*c* of the cartomizer 30, the second electrical circuit 34 is completed so the atomizer 42 receives power from the battery 5. The controller 28 control the switches 51, 52 to either make the first electrical circuit 32 so as to interrogate the resistor 40 and identify the cartomizer model, or to make the second electrical circuit 34 so as to operate the atomizer 42. In some cases, both switches 51, 52 might be closed to complete both the first and second circuits 32, 34 simultaneously.

Figure 5:
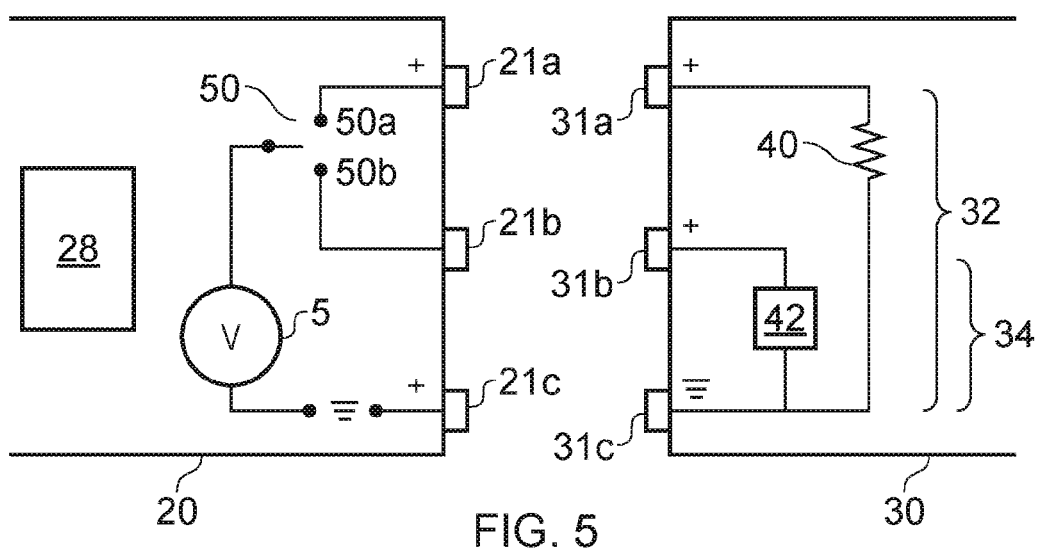

FIG. 5 shows a schematic representation of a second example vapor provision system configured for operation via three electrical connection terminals, the switching arrangement located in the control unit. The cartomizer 30 is configured as in the FIG. 4 example, so that the first electrical circuit 32 contains the resistor 40 in series between a first terminal 31*a* and a shared third earth terminal 31*c*, and the second electrical circuit 34 contains the atomizer 42 in series between a second terminal 31*b* and the shared third terminal 31*c*. The control unit also has three corresponding electrical connection terminals 21*a*-21*c*. A switching arrangement 50 comprising a single three-position switch is arranged in series with a battery 5, between a third terminal 21c and a pair of terminals comprising a first terminal 21a and a second terminal 21b. In a neutral position (illustrated) the switch 50 is open and neither the first terminal 21a nor the second terminal 21b is connected to the battery 5. The switch can be moved also to a first position and second position. In the first position, it contacts a first switch terminal 50a to make a connection from the battery to the first terminal 21a of the control unit. When the cartomizer 30 is attached to the control unit 20, the first and third terminals 21a, 21c of the control unit connect with the first and third terminals 31a, 31c of the cartomizer 30 to complete the first electrical circuit so the resistor 40 receives electrical power from the battery 5. When the switch 50 is in the second position it contacts a second switch terminal 50b to make a connection from the battery 5 to the second terminal 21b of the control unit 20. When the cartomizer 30 is attached to the control unit 20, the second and third terminals 21b, 21c of the control unit 20 connect with the second and third terminals 31b, 31c of the cartomizer 30 to complete the second electrical circuit 34 so the atomizer 42 receives electrical power from the battery 5. The controller 28 operates the switch between the neutral, first and second positions to energize neither circuit, the first circuit 32 or the second circuit 34 depending on whether the vapor provision system is off, a resistor value determination is needed, or vapor generation is required.

The switch or switches of the switching arrangement 50 when located in the control unit may be differently arranged and different in quantity than in the FIGS. 4 and 5 examples, to achieve the same effect of connecting the battery to either the first electrical circuit or the second electrical circuit (or both in some circumstances and configurations) via two of the three electrical connection terminals. The switches can be any convenient type of electrical switch.

Figure 6:
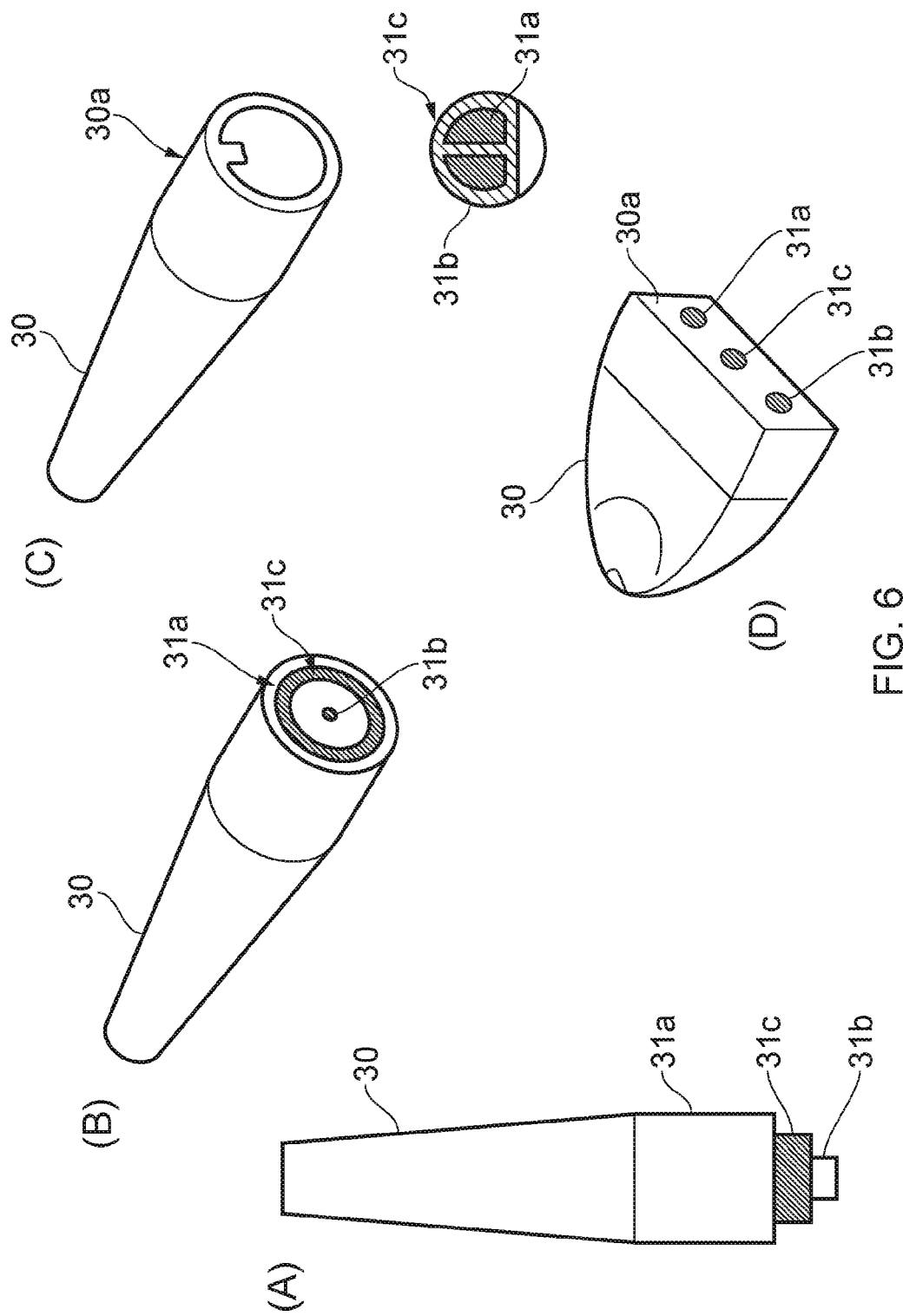

FIG. 6 shows perspective and plan exterior views of example cartomizers with three electrical connection terminals for connecting to a control unit. FIG. 6(A) shows a plan view of a cartomizer 30 in which the three terminals are configured in a co-axial stepped arrangement, with a central terminal 31b protruding furthest from an end face of the cartomizer 30 that engages with a control unit and being one of the two positive terminals. An outermost terminal 31a protrudes least from the end face of the cartomizer 30, and is the other positive terminal. A third terminal 31c is arranged between the outer and central terminals 31a, 31b, being the earth terminal. The cartomizer 30 may engage with a control unit via a screw fit or a push fit, for example.

FIG. 6(B) shows a perspective view of an example cartomizer 30 in which the three terminals are again coaxial, but are concentrically arranged in substantially the same transverse plan so that the end face of the cartomizer 30 is substantially flat. Again, the inner 31b and outer 31a terminals are configured as the positive connections for the first and second electrical circuits, and the intermediate terminal 31c provides the earth. A hybrid configuration in which one or two terminals are stepped as in FIG. 6(A) and the other two or one terminals are concentric in a flat plane as in FIG. 6(B) may also be used.

FIG. 6(C) shows a perspective view and an end view of a third example cartomizer in which the terminals 31a, 31b, 31c are positioned in an asymmetric arrangement on the end face of the cartomizer 30 in conjunction with an asymmetric shaping of the cartomizer end face 30a. This enables coupling of the cartomizer 30 to a control unit to be made orientation-dependent, in that the relative rotational positions of the two components must be properly matched to allow the mechanical and electrical connections to be made. This can assist in ensuring that the connections are properly made when the two components are brought together by a user. Any convenient asymmetric or non-symmetric configurations can be used, such as a D-shaped arrangement.

FIG. 6(D) shows a perspective end view of a further example cartomizer, for an electronic cigarette having an overall flattened shape (in contrast to the elongate substantially cylindrical examples of FIGS. 6(A) to 6(C)). A push fit can be used to join the cartomizer 30 to a control unit. The end face 30a of the cartomizer 30 is substantially flat. The three terminals 31a, 31b, 31c are individual button-shaped terminals spaced apart over the end face 30a. The illustrated example show the terminals in a regular straight-line array, but the positioning may be any regular or irregular array or scatter over the end face 30a. The earth terminal 31c is positioned between the two live terminals 31a, 31b, but this is an example only.

In any example, the three terminals may be differently designated between the positive and earth functions and between connection to the first and second electrical circuits.

Figure 7:
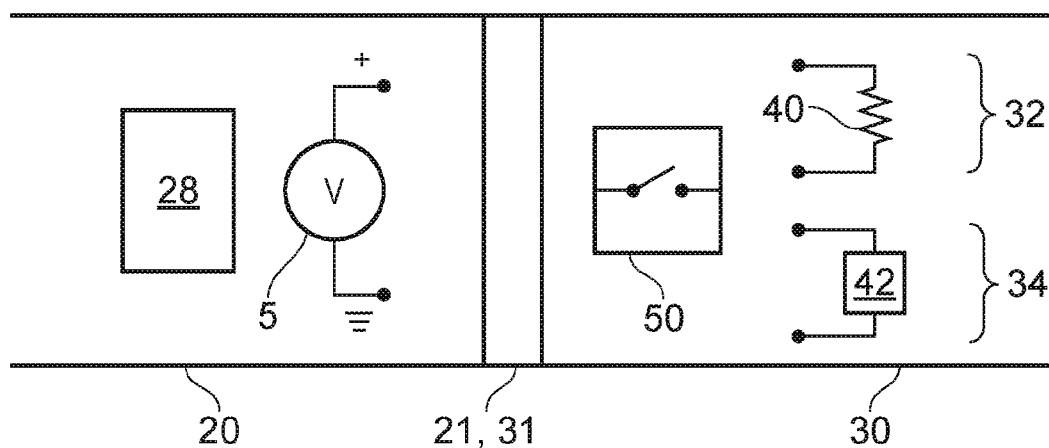

In some example devices, the switching arrangement 50 is included within the cartomizer 30. FIG. 7 shows a schematic representation of a vapor provision system configured with the switching arrangement 50 located in the cartomizer 30, and configured (by way of electrical connections which are not shown) to couple the battery 5 in the control unit 20 to either one of the first electrical circuit 32 or the second electrical circuit 34 in the cartomizer 30. This is achieved when the cartomizer 30 is attached to the cartomizer 30 using the mechanical and electrical cooperating engagement elements 21, 31, whereupon the controller 28 controls the switching arrangement 50 to make the appropriate connection of the battery 5 to the cartomizer 30 according to which of the first or second electric circuits 40, 42 is required to be operational.

Under such a configuration in which the switching arrangement 50 is inside the cartomizer 30, the first electrical circuit 32 and the second electrical circuit 34 may be implemented using two electrical connection terminals on the cartomizer for connection with two electrical connection terminals on the control unit when the cartomizer and the control unit are connected for operation of the vapor provision system. One of the terminals is a positive terminal and the other is an earth terminal. The switching arrangement 50 is placed between the terminals. The switching arrangement 50 comes under the control of the controller 28 in the control unit 20 when the cartomizer 30 and the control unit 20 are attached, and is configured to be switched between a first configuration that joins the first electrical circuit to both of the terminals so that power from the battery is directed to the identifier resistor 40, and a second configuration that joins the second electrical circuit to the terminals to that power from the battery is directed to the atomizer 42. In some examples, the switching arrangement may have a configuration to connect both circuits to the terminals; this may be one of the first or second configurations or a further additional configuration.

Figure 8:
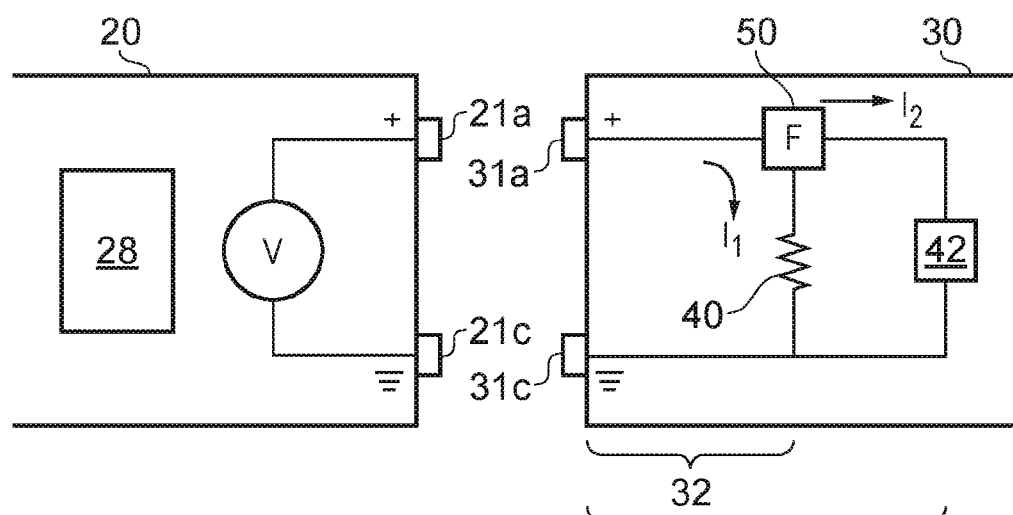

FIG. 8 shows a highly schematic representation of an example vapor provision system configured for operation via two electrical connection terminals and a switching arrangement located in the cartomizer. The switching arrangement 50 in this example comprises a field-effect transistor (FET), for example a metal-oxide-semiconductor field-effect transistor (MOSFET). A FET comprises a gate terminal, a source terminal and a drain terminal, plus a body terminal. The conductivity of the FET between the source and the drain is controlled by a voltage applied to the gate. A voltage below the gate threshold for a particular FET has little or no effect and there is no conductive path between the source and the drain. The FET therefore acts as an open or "off" switch. A voltage above the gate threshold creates a field which acts on the electrons in the device to induce a conductive path between the source and the drain. The FET therefore acts as a closed or "on" switch. The gate threshold voltage may be referred to as the switching voltage. Therefore, by application of an appropriate voltage from the battery 5 in the control unit 20 to the gate of the FET 50 in the cartomizer 30, the FET 50 can be closed or opened, and used to switch between the first electrical circuit 32 and the second electrical circuit 34. In the FIG. 8 example, the FET 50 is arranged so that when the controller 28 causes the battery 5 to apply a voltage below the gate threshold voltage to the gate of the FET 50, there is no current path for the second electric circuit 34, and instead, electrical power is directed from the terminals 31a, 31c via a first current path I1 through the first electric circuit 32 so that power is provided to the first electrical circuit 32 allowing the resistance of the identifier resistor 40 to be determined. When vapor generation is required, the controller 28 causes the battery 5 to apply a higher voltage, above the gate threshold voltage, to the gate of the FET 50. This opens the current path 12 between the source and the drain of the FET 50, which connects the second electrical circuit 34 to the terminals 31a, 31c. Power is thereby provided to the atomizer 42 and vapor is generated as the heating element of the atomizer 42 increases in temperature. This operation has the FET running in a so-called "enhancement mode", where the applied voltage increases the electrical conductivity to open the source-drain channel. The FET may alternatively be run in "depletion mode", in which the applied voltage decreases the conductivity to close the source-drain channel. In this case, the FET can be arranged so that the first electrical circuit 32 is connected to the terminals 31a, 31c when the source-drain channel is open, and the second electrical circuit 34 is connected to the terminals 31a, 31c when the source-drain channel is closed. In either case, the identifier resistor 40 in the first electric circuit is accessed when the applied voltage is below the FET's switching voltage, and the atomizer 42 in the second electrical circuit 34 is accessed when the applied voltage is above the FET's switching voltage.

Use of a FET in the cartomizer to implement the switching arrangement that selects between the identifier resistor and the atomizer's vapor generating element allows the cartomizer to be configured using two electrical contact terminals as is a common arrangement in cartomizer design. The presence of the FET introduces only minimal losses when the vapor generating element is activated. The switching voltage provides a pre-defined operational parameter for selecting between the first and second electrical circuits, so the cartomizer can be simply placed in one or other of an identification or cartomizer sensing mode and a vapor generation mode.

Figure 9:
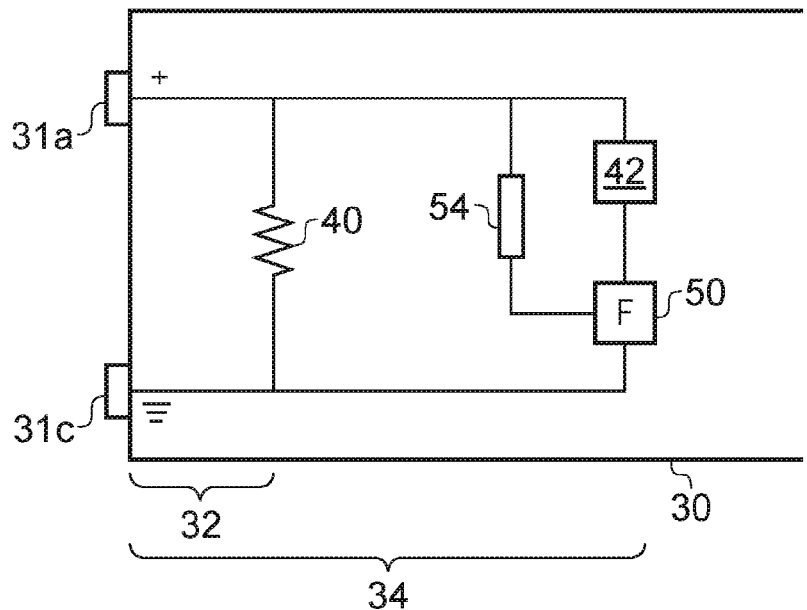
FIG. 9 shows an example circuit diagram of a circuit for including a field-effect transistor in a cartomizer.

FIG. 9 shows highly schematic representation of a second example of a cartomizer with two electrical connection terminals and a switching arrangement comprising a FET. As before, the cartomizer includes a first electrical circuit 32 with an identifier resistor 40, and a second electrical circuit 34 with an atomizer 42 which comprises a resistive load such as a heater. The second electrical circuit 34 is configured in parallel to the first electrical circuit 32, so that both circuits are across the positive electrical connection terminal 31a and the negative or ground electrical connection terminal 31c. The second electrical circuit 34 also comprises a FET such as a MOSFET representing at least part of a switching arrangement 50 and disposed in series with the atomizer 42. It also includes an optional pull-up resistor 54 which causes the gate voltage of the FET to increase (or be pulled up high). As an example, the atomizer 42 resistive load may have a resistance value of 3 kilo-ohms, the identifier resistor 40 may have a resistance value of 1 ohm, and the pull-up resistor 54 may have a resistance value of 11.3 ohms, although it should be appreciated that these values are exemplary only and other resistance values may be used instead.

In a first mode of operation, power is supplied from a battery in a control unit via the connection terminals 31a, 31c (not shown in FIG. 9, but may be configured as in FIG. 8, for example), as a DC voltage (for example) having a magnitude below the gate threshold voltage of the FET 50. The FET 50 is therefore not switched on, and power is supplied only through the first electrical circuit 32 with the identifier resistor 40. The "off" status of the FET 50 prevents the flow of current through the second electrical circuit 34. As described above, this allows an identification of the cartomizer to be made from a measurement of the resistance value of the identifier resistor 40.

In a second mode of operation, power is supplied via a voltage in excess of the gate threshold, to switch the FET 50 on. This may be via pulse width modulation (PWM) where the duty cycle is controlled (by a controller in the control unit for example) to select the average power (or average voltage or average current) supplied to the cartomizer 30. The "on" status of the FET 50 enables power to be delivered through the second circuit 34 to operate the atomizer 42, so that aerosol is generated from aerosolizsable substrate material. It should be appreciated that the average power supplied to the atomizer 42 (which determines the temperature in configurations where the atomizer 42 includes a heater) can be varied by varying the PWM duty cycle to modify the power at levels exceeding the gate threshold voltage of the FET 50.

Note that the parallel arrangement of the first and second circuits 32, 34 combined with the location of the FET 50 within the second circuit means that in the second mode, power is supplied to the first electrical circuit 32 as well as the second electrical circuit 34. However, the first mode is distinguished by the use of supply power to determine a value of the identifier resistor 40. This procedure need not be performed within the second mode which is for the purpose of operating the atomizer 42.

According to the above-mentioned examples, the inclusion of an identifier resistor in a cartomizer, the resistance value of which is determined and matched to a known cartomizer model, allows as many cartomizer models to be identified as there are available resistors with resistance values that can be accurately distinguished or resolved by the controller. While resistors are readily available with tight tolerance on the resistance values (in other words, the resistors are manufactured with an actual resistance value that matches the intended resistance value with a high degree of accuracy, for example to within 1%), it is nevertheless useful to select a set of identifier resistors with a separation between adjacent resistance values that is greater than the tolerance to ensure that any given resistance value can be properly identified and not confused with a neighboring value included in the resistor set.

If desired, the size of the identifier resistor set can be increased by also utilizing the resistance value of the vapor generating component. This can allow a larger number of different cartomizer models to be uniquely identifiable. For example, if the vapor generating component is a heating element in the form of a resistive coil, or a resistive mesh, or other electrically resistive component through which a current can be passed, the control unit can be configured to measure the resistance of the vapor generating element when the second electrical circuit is connected to the battery. Thus, two resistance values are obtained by interrogating the circuitry in the cartomizer, namely the resistance of the identifier resistor and the resistance of the vapor generating element. If a selection of vapor generating components are available with different resistance values, these values can be used to extend the size of the set of available resistance value characteristics for the cartomizers, so that a larger number of cartomizer models can be identified. When the two resistance values are combined in pairs, the set size is multiplied. For example, if 50 different identifier resistor values are combined with 4 different heating coil resistances, a total of 200 different combinations can be made. The inclusion of the heating coil resistance increases the set size by 4. Each combination of the two resistance values can be treated as a wholly separate identifier for a cartomizer as a whole. Alternatively, separate characteristics of a cartomizer model can be encoded using the two resistance values. For example, cartomizers may be provided with source liquid of different flavors and different nicotine strengths, with each flavor available in one or more nicotine strengths. The cartomizers may be configured such that the identifier resistor value indicates or is mapped to the flavor and the vapor generating element value indicates or is mapped to the nicotine strength. Clearly, other pairs of cartomizer features or characteristics can be represented or encoded by pairs of resistance values in this way.

Also, the mere presence of two resistance values can be used as a cartomizer identifier per se. The two values may be selected to have a particular characteristic relationship, such as differing by a significant amount. For example, the vapor generating element has a resistance value at least two times or at least five times or at least ten times the value of the identifier resistor (or vice versa, or with other multiples). The detection of two widely separated resistance values can then be used as an indicator of cartomizer origin, such as to test for genuine components. If the control unit finds that the cartomizer does not provide two resistance values that satisfy a pre-existing condition or relationship such as a minimum difference between the two resistance values, it can disable further operation of the electronic cigarette with that particular cartomizer. In this way, the electronic cigarette can be limited to functioning only with approved cartomizers.

In addition, the fact that two separate resistance values are detected, regardless of the differences in the resistance values, may signify the presence of an approved or authorized cartomizer. For example, if a user attempts to use a cartomizer that does not include an identifier resistor, the controller can only detect one resistance value when interrogating the circuitry of the cartomizer. Operation of the atomizer can be restricted such that it is only enabled when two resistance values are detected, and an unapproved cartomizer lacking an identifier resistor will therefore not be operated for aerosol generation. In this way, the electronic cigarette can be limited to functioning only with approved cartomizers and/or cartomizers including an identifier resistor.

Figure 10:
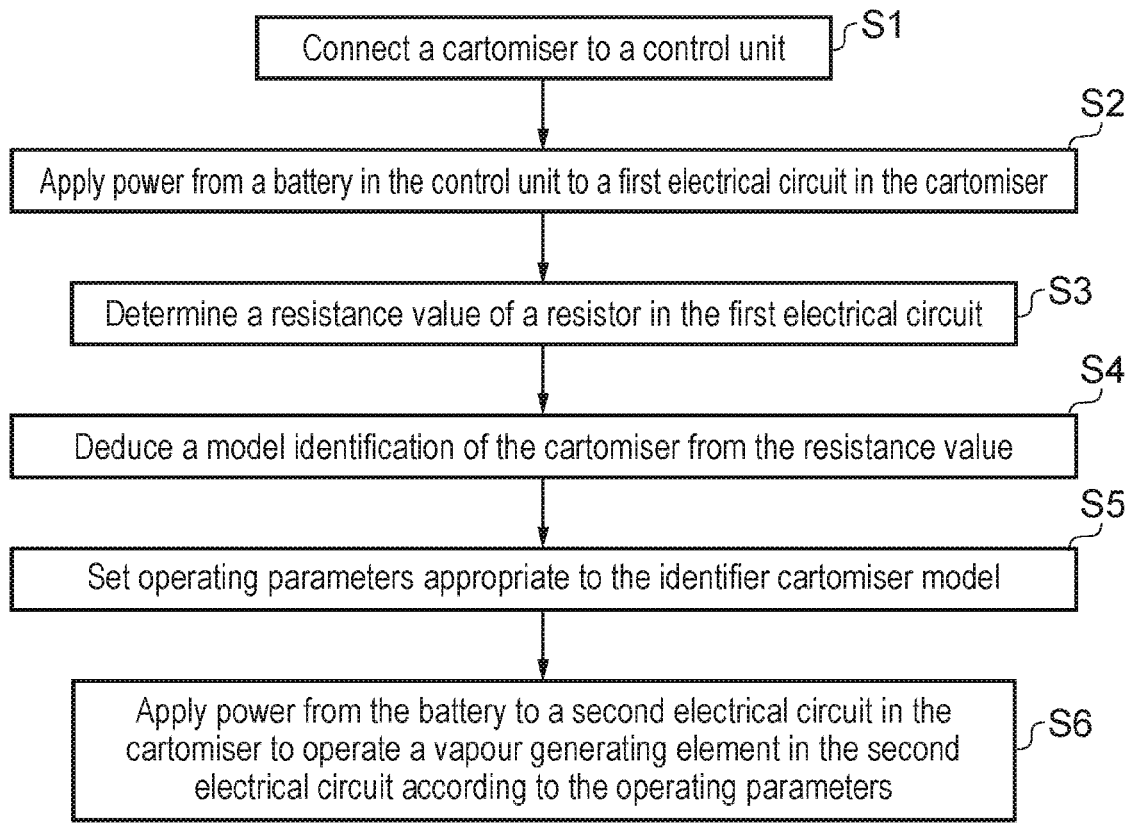
FIG. 10 shows a flow diagram of an example method for cartomizer detection.

FIG. 10 shows a flow chart of an example method of operating a vapor provision system having an identifier resistor. In S1, a cartomizer is connected to a control unit to form a vapor generating system such as an electronic cigarette. In S2, power is provided from a battery which may be in the control unit to a first electrical circuit in the cartomizer, where the first electrical circuit includes an identifier resistor having a resistance value unique to a model of the cartomizer. A control unit may be provided to control this power application. In S3, a value of the resistance of the identifier resistor is determined from parameters measured during the power provision (voltage and/or current). Again, the control unit may perform this task, followed by S4 in which a model of the cartomizer is deduced from the determined resistance value. For example, the control unit may access a look-up table that cross-references resistance values to cartomizer models. Once the cartomizer model has been identified, the vapor provision system is available for vapor generation. In an optional S5, the control unit may set operating parameters for the vapor provision system according to the model of the cartomizer, such as controlling the duration and level of electrical power provided for vapor generation, or determining that the cartomizer model is not allowable for use with the control unit so that further operation is disabled. Assuming that the system is not disabled in S5, the method continues to S6 in which power is applied to a second electrical circuit in the cartomizer to operate a vapor generating element in the second electrical circuit, such as a heating element, heating coil, heating mesh or vibrating plate. The power may be applied in accordance with any operating parameters set in S5.

Note that any practical technique can be used for determining/ascertaining/deducing/measuring the resistance value of the identifier resistor in a first mode of operation. This includes the measurement of a voltage dropped across the identifier resistor for a fixed current passed through it, and the converse arrangement of measuring the current drawn by the identifier resistor when a fixed voltage is applied across it, and in either case calculating resistance from Ohm's law according to R=V/I.

The present disclosure is not limited to the use of an identifier resistor included a cartomizer for the purpose of identifying a cartomizer model from a resistance value of the identifier resistor. Other electrically-readable or addressable elements may be used, which carry a characteristic which may be usable to identify the model of the cartomizer or to determine other properties of the cartomizer. In general terms, such an element can be considered as a characteristic-carrying element. As an example, the cartomizer may include a readable memory that stores data from which the model or identity of the cartomizer can be determined (identifier data, comparable to the resistor value of a resistor used as a characteristic-carrying element) and/or from which other properties of the cartomizer can be determined, such as location of the device, type and/or amount of aerosolizsable substrate material, and manufacturing or manufacture information.

In such examples, the identifier resistor described above as being comprised in the first electrical circuit of the cartomizer is replaced with a readable memory storing data corresponding to one or more characteristics and which can be read by providing electrical power to the first electrical circuit.

Figure 11:
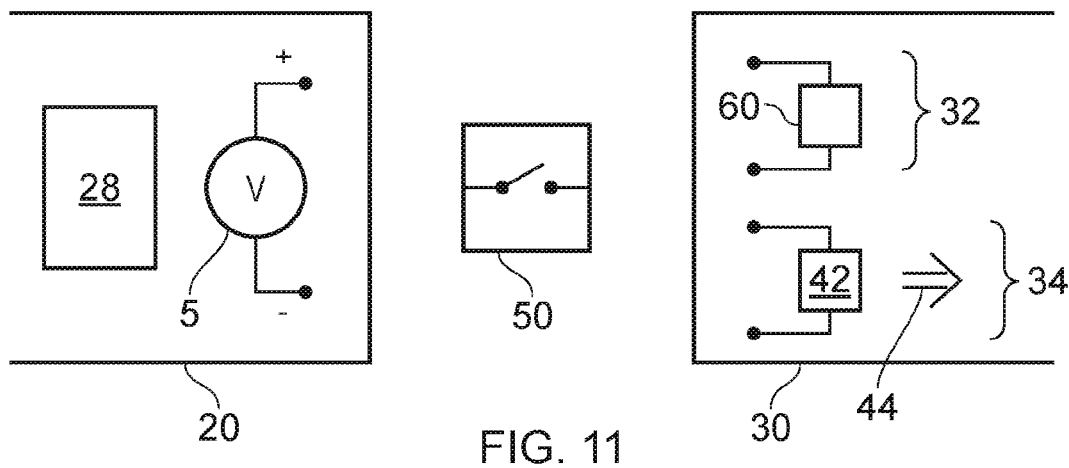
FIGS. 11 to 17 shows schematic representations of parts of cartomizers and control units according to examples comprising a readable memory characteristic-carrying element.

FIG. 11 shows a schematic representation of a vapor provision system similar to that of FIG. 2, in which the identifier resistor 40 in the first electrical circuit 32 is replaced with a readable memory 60. As before, the control unit 20 and the cartomizer 30 are connectable via a switching arrangement 50 for applying power to one or both of the first electrical circuit 32 and the second electrical circuit 34 including the atomizer 42. Operation may be the same as for the FIG. 2 example, where electrical power is applied to the first electrical circuit to determine a characteristic of the readable memory 60 (stored as data in the memory) instead of the resistance characteristic of the FIG. 2 resistor 40.

Figure 12:
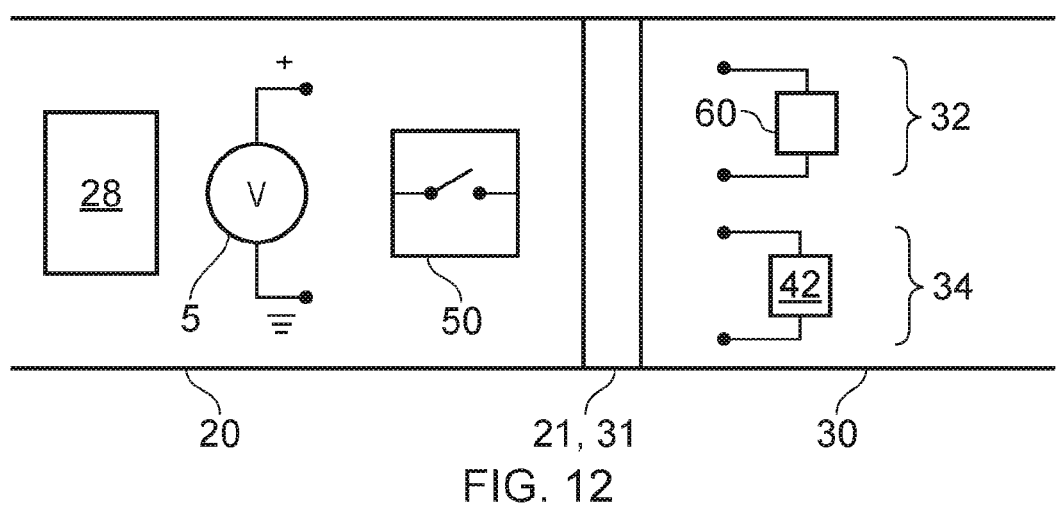

FIG. 12 shows a schematic representation of a vapor provision system configured as the FIG. 3 example except that the first electrical circuit 32 includes a readable memory 60 in place of the resistor 40. The switching arrangement 50 is in the control unit 20 and operates as in the FIG. 3 example to apply power to the first electrical circuit 32 and/or the second electrical circuit 34.

Figure 13:
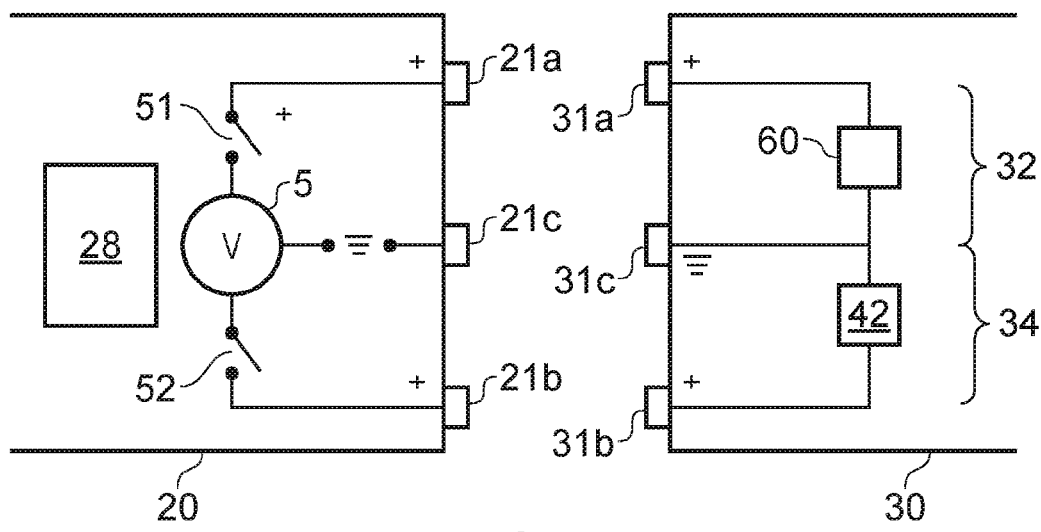
Figure 14:
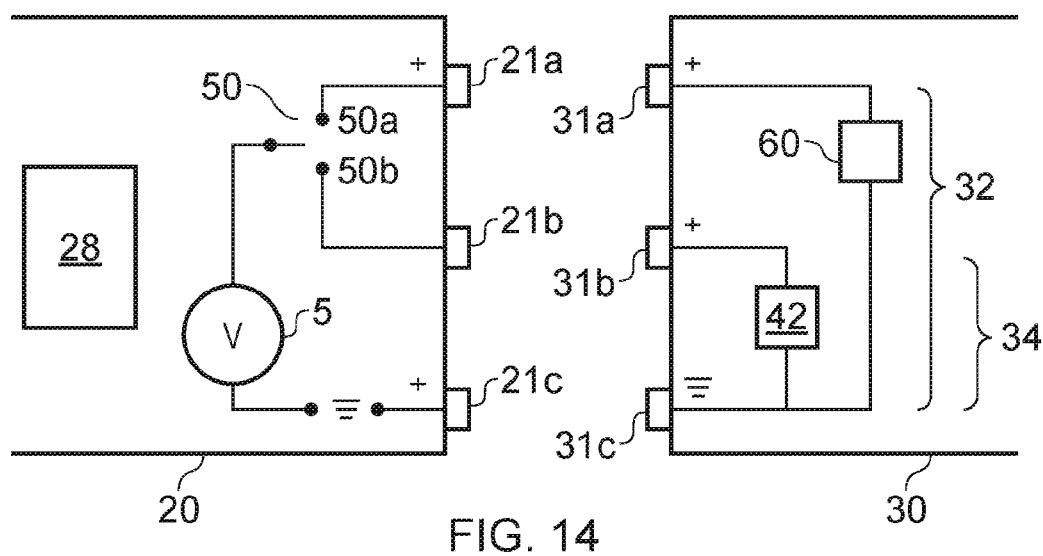

FIGS. 13 and 14 shows schematic representations of vapor provision systems configured respectively as the FIGS. 4 and 5 examples, with the switching arrangement in the control unit 20 and three electrical connection terminals between the control unit 20 and the cartomizer 30. The first electrical circuit 32 in the cartomizer 30 comprises a readable memory 60 in place of the resistor 40 in the FIGS. 4 and 5 examples. Otherwise, operation is as described for FIG. 4 and FIG. 5 respectively.

Figure 15:
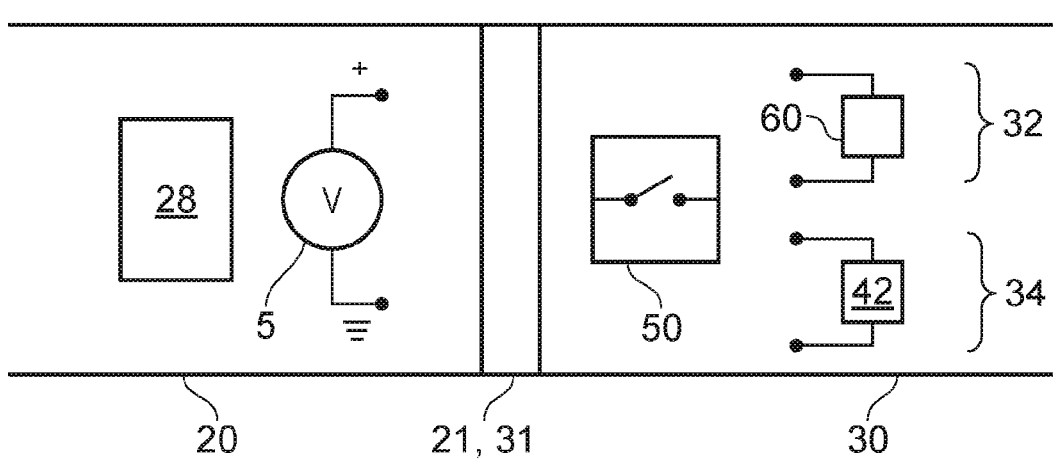

FIG. 15 shows a schematic representation of a vapor provision system similar to the FIG. 7 example, where the switching arrangement 50 is located in the cartomizer 30. The resistor 40 of the FIG. 7 example is replaced with a readable memory 60 in the first electrical circuit 32. Operation is as described with respect to FIG. 7 for the purpose of determining one or more characteristics of the readable memory 60, stored as data.

Figure 16:
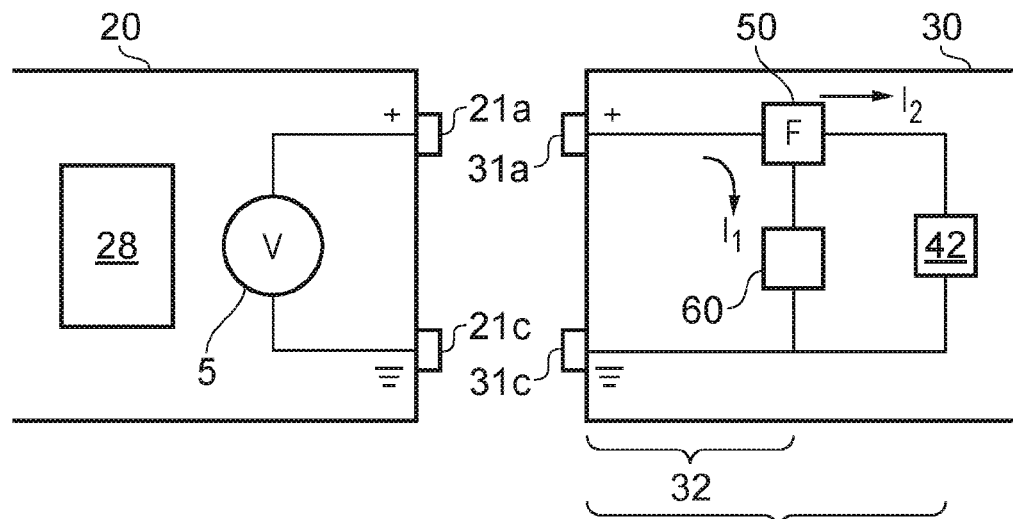

FIG. 16 shows a schematic representation of a vapor provision system configured as the FIG. 8 example, having two electrical connection terminals between the control unit 20 and the cartomizer 30, and a switching arrangement 50 implemented using a field-effect transistor. As in the immediately preceding examples, the resistor 40 in the first electrical circuit 32 of FIG. 8 is replaced with a readable memory 60. Operation is as described with respect to FIG. 8.

Figure 17:
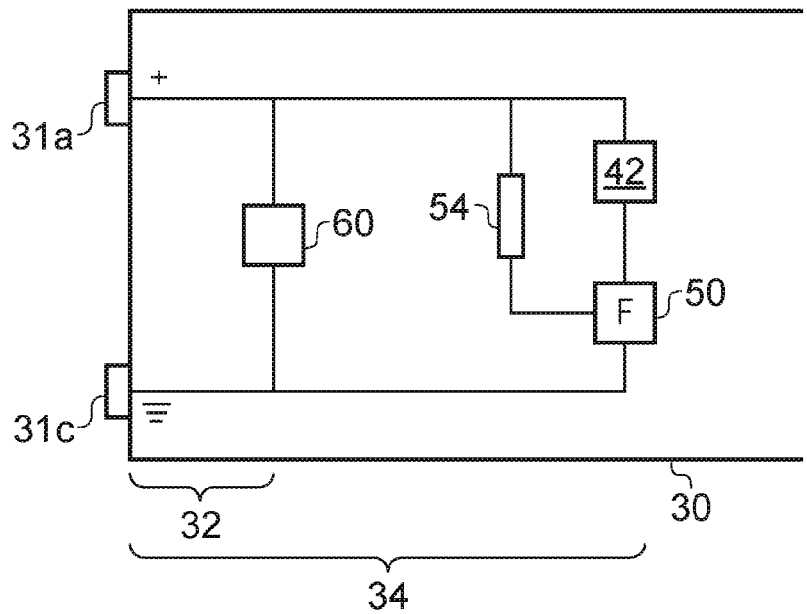

FIG. 17 shows a schematic representation of an alternative format of cartomizer with two electrical connections and a FET switching arrangement 50. It corresponds to the example of FIG. 9 save for the substitution of the resistor 40 in the first electrical circuit 32 with a readable memory 60. Operation is as described with respect to FIG. 9.

Figure 18:
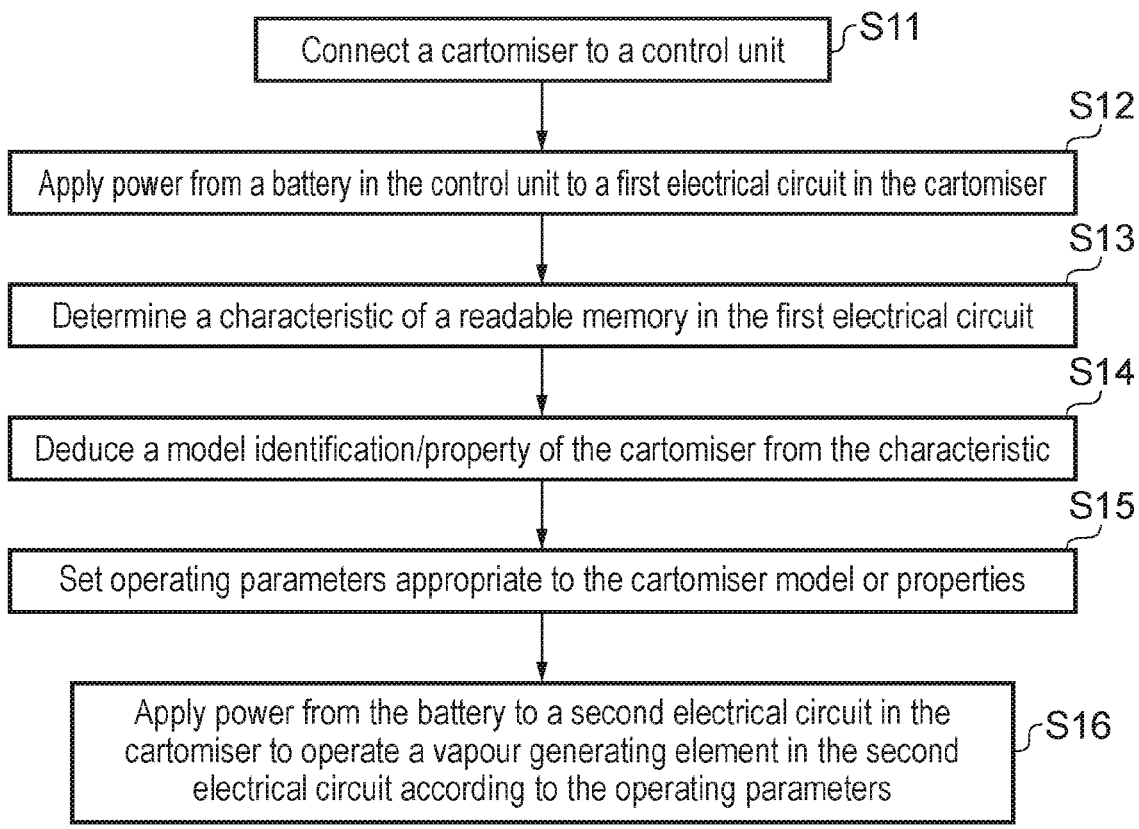
FIG. 18 shows a flow diagram of another example method.

FIG. 18 shows a flow chart of an example method of operating a vapor provision system having a characteristic-carrying element in the form of a readable memory. In S11, a cartomizer is connected to a control unit to form a vapor generating system such as an electronic cigarette. In S12, power is provided from a battery which may be in the control unit to a first electrical circuit in the cartomizer, where the first electrical circuit includes a readable memory having one or more characteristics in the form of stored data corresponding to one or more properties of the cartomizer. The characteristic may or may not be identifier data unique to a model of the cartomizer. A control unit may be provided to control this power application. In S13, the characteristic data of the readable memory is determined from results of the power provision. Again, the control unit may perform this task, followed by S14 in which a model or other property or properties of the cartomizer is deduced from the determined characteristic data. The data may directly indicate the properties, or the properties may need to be determined using the data. For example, the control unit may access a look-up table that cross-references characteristic data to cartomizer models or other cartomizer properties.

Once the cartomizer model or properties have been identified or determined, the vapor provision system is available for vapor generation. In an optional S15, the control unit may set operating parameters for the vapor provision system according to the model and/or properties of the cartomizer, such as controlling the duration and level of electrical power provided for vapor generation, or determining that the cartomizer model is not allowable for use with the control unit so that further operation is disabled. Assuming that the system is not disabled in S15, the method continues to S16 in which power is applied to a second electrical circuit in the cartomizer to operate a vapor generating element in the second electrical circuit, such as a heating element, heating coil, heating mesh or vibrating plate. The power may be applied in accordance with any operating parameters set in S15.

Although the above description refers to cartomizers as examples of aerosolizsable substrate material carrying portions, it should be appreciated that, in other implementations, other examples of aerosolizsable substrate material carrying portions may be used with a correspondingly adapted control unit. For example, in systems configured to generate a vapor for inhalation by heating a solid/gel substrate, the aerosolizsable substrate material carrying portion may be configured as a carrier material (e.g. paper, card) having a solid/gel substrate material as an aerosolizsable substrate material disposed thereon/therein. The carrier material in this example additionally comprises the first and second electrical circuits, e.g. forming part of the carrier material or placed on a surface thereof. The second electrical circuit comprising the vapor generating element (atomizer) can be arranged to be in contact with, or in proximity to, the aerosolizsable substrate material. In accordance with the principles of the present disclosure, the electrical circuits comprise electrical contacts which can electrically couple to a control unit when the aerosolizsable substrate material carrying portion is received in/coupled to the control unit.

In conclusion, in order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein. The disclosure may include other inventions not presently claimed, but which may be claimed in future.

Further particular and preferred aspects of the invention are set out in the accompanying independent and dependent clauses. Features of the dependent clauses may be combined with those of the independent clauses and independent claims as appropriate and in combinations other than those explicitly set out in the clauses and claims.

1. An electronic vapor provision system comprising: a control unit configured to provide power from a battery in the control unit to components of the system, and comprising a controller configured to control components of the system; and an aerosolizsable substrate material carrying portion separably connectable to the control unit to obtain power from the battery, and comprising: a first electrical circuit including an identifier resistor; and a second electrical circuit including a vapor generating element configured to generate an inhalable vapor from an aerosolizsable substrate material; wherein: the second electrical circuit can be selectively provided with power from the battery when power is supplied to the aerosolizsable substrate material carrying portion; and the controller is configured to operate in a first mode in which a resistance value for the identifier resistor is determined by providing power from the battery to the first electrical circuit, and in a second mode in which the vapor generating element is operated by providing power from the battery to the second electrical circuit.

2. An electronic vapor provision system according to clause 1, wherein the controller is configured to identify the aerosolizsable substrate material carrying portion from the resistance value of the identifier resistance.

3. An electronic vapor provision system according to clause 1 or clause 2, comprising a switching arrangement operable by the controller to selectively provide power from the battery to the second electrical circuit.

4. An electronic vapor provision system according to clause 3, wherein the switching arrangement is located in the control unit.

5. An electronic vapor provision system according to clause 4, wherein: the aerosolizsable substrate material carrying portion comprises three electrical connection terminals for connection with the control unit, the electrical connection terminals comprising a first electrical connection terminal for providing power to the first electrical circuit, a second electrical connection terminal for providing power to the second electrical circuit, and a third electrical connection terminal comprising an electrical earth connection shared by the first electrical circuit and the second electrical circuit; and the control unit comprises three electrical connection terminals for connection with the aerosolizsable substrate material carrying portion, the switching arrangement configured to switch between connecting the first electrical connection terminal with the battery and connecting the second electrical connection terminal with the battery.

6. An electronic vapor provision system according to clause 5, wherein the three electrical connection terminals of the aerosolizsable substrate material carrying portion are disposed on a face of the aerosolizsable substrate material carrying portion in a concentric arrangement, a co-axial arrangement or in a regular or irregular array.

7. An electronic vapor provision system according to any one of clauses 1 to 3, wherein the switching arrangement is located in the aerosolizsable substrate material carrying portion.

8. An electronic vapor provision system according to clause 7, wherein the aerosolizsable substrate material carrying portion comprises two electrical connection terminals for connection with the control unit, the electrical connection terminals comprising an electrical connection terminal for providing power to the first electrical circuit and the second electrical circuit, and an electrical earth connection for the first electrical circuit and the second electrical circuit, and the switching arrangement is configured to switch between connecting the first electrical circuit with the said electrical connection terminal and connecting the second electrical circuit with the said electrical connection terminal.

9. An electronic vapor provision system according to clause 8, wherein the switching arrangement comprises a field-effect transistor configured as a switch operable to provide power from the battery to the second electrical circuit in accordance with a voltage level set by the controller.

10. An electronic vapor provision system according to clause 9, wherein the field-effect transistor switches power to the second electrical circuit according to an applied voltage level which is less than a gate threshold voltage of the field-effect transistor, or equal to or above the gate threshold value.

11. An electronic vapor provision system according to clause 7, wherein the field-effect transistor provides power to the second electrical circuit when the applied voltage level is equal to or above the gate threshold value.

12. An electronic vapor provision system according to any one of clauses 9 to 11, wherein the field-effect transistor comprises a metal-oxide-semiconductor field-effect transistor.

13. An electronic vapor provision system according to any preceding claim, wherein the controller is further configured to determine a resistance value for the vapor generating element when power is provided to the second electrical circuit, and to identify the aerosolizsable substrate material carrying portion from the resistance value of the identifier resistor and the resistance value of the vapor generating element.

14. An electronic vapor provision system according to any one of clauses 2 to 13, wherein the controller is configured to control components of the system according to the determined identity of the aerosolizsable substrate material carrying portion.

15. An electronic vapor provision system according to any one of the preceding clauses, wherein the aerosolizsable substrate material carrying portion is a cartomizer.

16. An electronic vapor provision system according to clause 15, wherein the controller is configured to deduce a model identification of the cartomizer from the resistance value determined for the identifier resistor.

17. An aerosolizsable substrate material carrying portion for an electronic vapor provision system, separably connectable to a control unit to obtain power from a battery within the control unit, and comprising: a first electrical circuit including an identifier resistor; and a second electrical circuit including a vapor generating element configured to generate an inhalable vapor from an aerosolizsable substrate material when provided with power from the battery; wherein the second electrical circuit can be selectively provided with power from the battery when power is supplied to the aerosolizsable substrate material carrying portion for the purposes of operating in a first mode in which a resistance value of the identifier resistor is determined when power is provided from the battery to the first electrical circuit, and for the purpose of operating in a second mode in which the vapor generating element is operated when power is provided from the battery to the second electrical circuit.

18. A control unit for an electronic vapor provision system which is separably connectable to an aerosolizsable substrate material carrying portion comprising a first electrical circuit including an identifier resistor and a second electrical circuit including a vapor generating element configured to generate an inhalable vapor from an aerosolizsable substrate material, the second electrical circuit selectively providable with power from the battery when power is supplied to the aerosolizsable substrate material carrying portion, the control unit configured to provided power from a battery in the control unit to components of the vapor provision system, and comprising: a controller configured to control components of the system and to operate in a first mode in which power is provided from the battery to the first electrical circuit to determine a resistance value for the identifier resistor, and to operate in a second mode in which power is provided from the battery to the second electrical circuit to operate the vapor generating element.

19. A controller for an electronic vapor provision system comprising a control unit and an aerosolizsable substrate material carrying portion separably connectable to the control unit, the controller configured to: provide power from a battery in the control unit to a first electrical circuit in the aerosolizsable substrate material carrying portion including an identifier resistor and to a second electrical circuit in the aerosolizsable substrate material carrying portion including a vapor generating element configured to generate an inhalable vapor from an aerosolizsable substrate material; determine a resistance value for the identifier resistor when power is provided to the first electrical circuit; and operate the vapor generating element when power is provided to the second electrical circuit.

20. A method of operating an electronic vapor provision system comprising: connecting an aerosolizsable substrate material carrying portion to a control unit; providing power from a battery in the control unit to a first electrical circuit in the aerosolizsable substrate material carrying portion, the first electrical circuit including an identifier resistor; determining a resistance value of the identifier resistor; deducing an identity of the aerosolizsable substrate material carrying portion from the resistance value; and providing power from the battery in the control unit to a second electrical circuit in the aerosolizsable substrate material carrying portion including a vapor generating element to operate the vapor generating element to generate an inhalable vapor from an aerosolizsable substrate material.

The invention claimed is:

1. An electronic vapor provision system comprising:
   a control unit configured to provide power from a battery in the control unit to components of the electronic vapor provision system, and comprising a controller configured to control components of the electronic vapor provision system;
   an aerosolizable substrate material carrying portion separably connectable to the control unit to obtain power from the battery, and comprising:
      a first electrical circuit including a characteristic-carrying element; and
      a second electrical circuit including a vapor generating element configured to generate an inhalable vapor from an aerosolizable substrate material;
   wherein:
      the second electrical circuit can be selectively provided with power from the battery when power is supplied to the aerosolizable substrate material carrying portion; and
      the controller is configured to operate in a first mode in which a characteristic of the characteristic-carrying element is determined by providing power from the battery to the first electrical circuit, and in a second mode in which the vapor generating element is operated by providing power from the battery to the second electrical circuit; and
   a switching arrangement operable by the controller to selectively provide power from the battery to the second electrical circuit, wherein:
      the switching arrangement is located in the aerosolizable substrate material carrying portion, and
      the aerosolizable substrate material carrying portion comprises two electrical connection terminals for connection with the control unit, the two electrical connection terminals comprising a first electrical connection terminal for providing power to the first electrical circuit and the second electrical circuit, and an electrical earth connection for the first electrical circuit and the second electrical circuit, and the switching arrangement is configured to switch between connecting the first electrical circuit with the first electrical connection terminal and connecting the second electrical circuit with the first electrical connection terminal.

2. The electronic vapor provision system according to claim 1, wherein the characteristic-carrying element is a characteristic-carrying identifier element comprising an identifier resistor, and the characteristic is a resistance value of the identifier resistor.

3. The electronic vapor provision system according to claim 1, wherein the characteristic-carrying element is a characteristic-carrying identifier element comprising readable memory, and the characteristic is identifier data stored in the readable memory.

4. The electronic vapor provision system according to claim 2, wherein the controller is configured to identify the aerosolizable substrate material carrying portion from the characteristic of the characteristic-carrying identifier element.

5. The electronic vapor provision system according to claim 1, wherein the characteristic-carrying element is a readable memory, and the characteristic is property data stored in the readable memory.

6. The electronic vapor provision system according to claim 5, wherein the controller is configured to obtain one or more properties of the aerosolizable substrate material carrying portion from the property data.

7. The electronic vapor provision system according to claim 1, wherein the switching arrangement comprises a field-effect transistor configured as a switch operable to provide power from the battery to the second electrical circuit in accordance with a voltage level set by the controller.

8. The electronic vapor provision system according to claim 7, wherein the field-effect transistor switches power to the second electrical circuit according to an applied voltage level which is less than a gate threshold voltage of the field-effect transistor, or equal to or above the gate threshold voltage value.

9. The electronic vapor provision system according to claim 8, wherein the field-effect transistor provides power to the second electrical circuit when the applied voltage level is equal to or above the gate threshold voltage.

10. The electronic vapor provision system according to claim 7, wherein the field-effect transistor comprises a metal-oxide-semiconductor field-effect transistor.

11. The electronic vapor provision system according to claim 1, wherein the controller is further configured to determine a resistance value for the vapor generating element when power is provided to the second electrical circuit, and to identify the aerosolizable substrate material carrying portion from the characteristic of the characteristic-carrying element and the resistance value of the vapor generating element.

12. The electronic vapor provision system according to claim 2, wherein the controller is configured to control components of the electronic vapor provision system according to the determined identity or properties of the aerosolizable substrate material carrying portion.

13. The electronic vapor provision system according to claim 1, wherein the aerosolizable substrate material carrying portion is a cartomizer.

14. The electronic vapor provision system according to claim 13, wherein the controller is configured to deduce a model identification of the cartomizer from the characteristic determined for the characteristic-carrying element.

15. An aerosolizable substrate material carrying portion for an electronic vapor provision system, separably connectable to a control unit to obtain power from a battery within the control unit, and comprising:
a first electrical circuit including a characteristic-carrying element;
a second electrical circuit including a vapor generating element configured to generate an inhalable vapor from an aerosolizable substrate material when provided with power from the battery, wherein the second electrical circuit can be selectively provided with power from the battery when power is supplied to the aerosolizable substrate material carrying portion for the purposes of operating in a first mode in which a characteristic of the characteristic-carrying element is determined when power is provided from the battery to the first electrical circuit, and for the purpose of operating in a second mode in which the vapor generating element is operated when power is provided from the battery to the second electrical circuit;
a switching arrangement operable by the controller to selectively provide power from the battery to the second electrical circuit; and
two electrical connection terminals for connection with the control unit, the two electrical connection terminals comprising a first electrical connection terminal for providing power to the first electrical circuit and the second electrical circuit, and an electrical earth connection for the first electrical circuit and the second electrical circuit, and the switching arrangement is configured to switch between connecting the first electrical circuit with the first electrical connection terminal and connecting the second electrical circuit with the first electrical connection terminal.

16. A control unit for an electronic vapor provision system which is separably connectable to an aerosolizable substrate material carrying portion comprising a first electrical circuit including a characteristic-carrying element and a second electrical circuit including a vapor generating element configured to generate an inhalable vapor from an aerosolizable substrate material, the second electrical circuit selectively providable with power from the battery when power is supplied to the aerosolizable substrate material carrying portion, the control unit configured to provide power from a battery in the control unit to components of the electronic vapor provision system, and comprising:
a controller configured to:
control components of the electronic vapor provision system and to operate in a first mode in which power is provided from the battery to the first electrical circuit to determine a characteristic of the characteristic-carrying element, and to operate in a second mode in which power is provided from the battery to the second electrical circuit to operate the vapor generating element, and
operate a switching arrangement in the aerosolizable substrate material carrying portion to selectively provide power from the battery to the second electrical circuit, the switching arrangement configured to switch between connecting the first electrical circuit with a first electrical connection terminal on the aerosolizable substrate material carrying portion and connecting the second electrical circuit with the first electrical connection terminal, wherein the aerosolizable substrate carrying portion has two electrical connection terminals for connection with the control unit comprising the first electrical connection terminal for providing power to the first electrical circuit and the second electrical circuit and an electrical earth connection for the first electrical circuit and the second electrical circuit.

17. A controller for an electronic vapor provision system comprising:
a control unit; and
an aerosolizable substrate material carrying portion separably connectable to the control unit,
wherein the controller is configured to:
provide power from a battery in the control unit to a first electrical circuit in the aerosolizable substrate material carrying portion including a characteristic-carrying element and to a second electrical circuit in the aerosolizable substrate material carrying portion including a vapor generating element configured to generate an inhalable vapor from an aerosolizable substrate material,
determine a characteristic of the characteristic-carrying element when power is provided to the first electrical circuit,
operate the vapor generating element when power is provided to the second electrical circuit,
operate a switching arrangement in the aerosolizable substrate material carrying portion to selectively provide power from the battery to the second electrical circuit, the switching arrangement configured to switch between connecting the first electrical circuit with a first electrical connection terminal on the aerosolizable substrate material carrying portion and connecting the second electrical circuit with the first electrical connection terminal, wherein the aerosolizable substrate carrying portion has two electrical connection terminals for connection with the control unit comprising the first electrical connection terminal for providing power to the first electrical circuit and the second electrical circuit and an electrical earth connection for the first electrical circuit and the second electrical circuit.

18. An electronic vapor provision system comprising:
a control unit configured to provide power from a battery in the control unit to components of the electronic vapor provision system, and comprising a controller configured to control components of the electronic vapor provision system;
an aerosolizable substrate material carrying portion separably connectable to the control unit to obtain power from the battery, and comprising:
a first electrical circuit including an identifier resistor, and
a second electrical circuit including a vapor generating element configured to generate an inhalable vapor from an aerosolizable substrate material, wherein the second electrical circuit can be selectively provided with power from the battery when power is supplied to the aerosolizable substrate material carrying portion,
wherein the controller is configured to operate in a first mode in which a resistance value for the identifier resistor is determined by providing power from the battery to the first electrical circuit, and in a second mode in which the vapor generating element is operated by providing power from the battery to the second electrical circuit; and a switching arrangement operable by the controller to selectively provide power from the battery to the second electrical circuit, wherein:

the switching arrangement is located in the aerosolizable substrate material carrying portion, and the aerosolizable substrate material carrying portion comprises two electrical connection terminals for connection with the control unit, the electrical connection terminals comprising a first electrical connection terminal for providing power to the first electrical circuit and the second electrical circuit, and an electrical earth connection for the first electrical circuit and the second electrical circuit, and the switching arrangement is configured to switch between connecting the first electrical circuit with the first electrical connection terminal and connecting the second electrical circuit with the first electrical connection terminal.

19. An electronic vapor provision system comprising:

a control unit configured to provide power from a battery in the control unit to components of the electronic vapor provision system, and comprising a controller configured to control components of the electronic vapor provision system;

an aerosolizable substrate material carrying portion separably connectable to the control unit to obtain power from the battery, and comprising:

a first electrical circuit including a readable memory, and a second electrical circuit including a vapor generating element configured to generate an inhalable vapor from an aerosolizable substrate material, wherein the second electrical circuit can be selectively provided with power from the battery when power is supplied to the aerosolizable substrate material carrying portion, wherein the controller is configured to operate in a first mode in which identity data identifying the aerosolizable substrate material carrying portion stored in the readable memory is determined by providing power from the battery to the first electrical circuit, and in a second mode in which the vapor generating element is operated by providing power from the battery to the second electrical circuit; and a switching arrangement operable by the controller to selectively provide power from the battery to the second electrical circuit, wherein:

the switching arrangement is located in the aerosolizable substrate material carrying portion, and the aerosolizable substrate material carrying portion comprises two electrical connection terminals for connection with the control unit, the electrical connection terminals comprising a first electrical connection terminal for providing power to the first electrical circuit and the second electrical circuit, and an electrical earth connection for the first electrical circuit and the second electrical circuit, and the switching arrangement is configured to switch between connecting the first electrical circuit with the first electrical connection terminal and connecting the second electrical circuit with the first electrical connection terminal.

20. An electronic vapor provision system comprising:

a control unit configured to provide power from a battery in the control unit to components of the electronic vapor provision system, and comprising a controller configured to control components of the electronic vapor provision system;

an aerosolizable substrate material carrying portion separably connectable to the control unit to obtain power from the battery, and comprising:

a first electrical circuit including a readable memory, and a second electrical circuit including a vapor generating element configured to generate an inhalable vapor from an aerosolizable substrate material, wherein the second electrical circuit can be selectively provided with power from the battery when power is supplied to the aerosolizable substrate material carrying portion, wherein the controller is configured to operate in a first mode in which property data indicating one or more properties of the aerosolizable substrate material carrying portion stored in the readable memory is determined by providing power from the battery to the first electrical circuit, and in a second mode in which the vapor generating element is operated by providing power from the battery to the second electrical circuit; and a switching arrangement operable by the controller to selectively provide power from the battery to the second electrical circuit, wherein:

the switching arrangement is located in the aerosolizable substrate material carrying portion, and the aerosolizable substrate material carrying portion comprises two electrical connection terminals for connection with the control unit, the electrical connection terminals comprising a first electrical connection terminal for providing power to the first electrical circuit and the second electrical circuit, and an electrical earth connection for the first electrical circuit and the second electrical circuit, and the switching arrangement is configured to switch between connecting the first electrical circuit with the first electrical connection terminal and connecting the second electrical circuit with the first electrical connection terminal.

* * * * *